US009358380B2

(12) United States Patent
Ivanoff et al.

(10) Patent No.: US 9,358,380 B2
(45) Date of Patent: Jun. 7, 2016

(54) METHODS AND SYSTEMS COMBINING AC ELECTROOSMOSIS WITH DIELECTROPHORESIS TO ENHANCE DELIVERY OF ACTIVE AGENTS INTO INTRAORAL STRUCTURES

(71) Applicant: University of Tennessee Research Foundation, Knoxville, TN (US)

(72) Inventors: Chris S. Ivanoff, Memphis, TN (US); Timothy L. Hottel, Memphis, TN (US); Franklin Garcia-Godoy, Memphis, TN (US)

(73) Assignee: University of Tennessee Research Foundation, Knoxville, TN (US)

( * ) Notice: Subject to any disclaimer, the term of this patent is extended or adjusted under 35 U.S.C. 154(b) by 0 days.

(21) Appl. No.: 14/092,269

(22) Filed: Nov. 27, 2013

(65) Prior Publication Data

US 2014/0162206 A1 Jun. 12, 2014

Related U.S. Application Data

(60) Provisional application No. 61/731,993, filed on Nov. 30, 2012.

(51) Int. Cl.
*A61C 19/06* (2006.01)
*A61N 1/04* (2006.01)
(Continued)

(52) U.S. Cl.
CPC ............ *A61N 1/0428* (2013.01); *A61C 19/063* (2013.01); *A61N 1/0548* (2013.01); *A61N 1/325* (2013.01); *A61C 8/0007* (2013.01); *A61N 1/044* (2013.01)

(58) Field of Classification Search
CPC . A61C 19/063; A61N 1/0428; A61N 1/0548; A61N 1/325

USPC ........................................................... 433/32
See application file for complete search history.

(56) References Cited

U.S. PATENT DOCUMENTS 3,207,161 A * 9/1965 Dietz ............................ 607/134
4,629,424 A * 12/1986 Lauks et al. ...................... 433/6
(Continued)

OTHER PUBLICATIONS

Ivanoff et al., "Dielectrophoresis enhances the whitening effect of carbamide peroxide on enamel," Am. J. Dent. vol. 24 pp. 259-263 (2011).

(Continued)

*Primary Examiner* — Cris L Rodriguez
*Assistant Examiner* — Hao D Mai
(74) *Attorney, Agent, or Firm* — Jenkins, Wilson, Taylor & Hunt, P.A.

(57) ABSTRACT

Methods and systems for delivering an active agent into an intraoral structure are disclosed. One embodiment of a method for implementing the subject matter described herein includes generating an electrical signal that includes a first frequency, a second frequency, and a third frequency, and supplying the electrical signal to an embedded circuit contained in an intraoral delivery tray, wherein the embedded circuit includes at least one electrode that includes projections positioned proximally to a surface of an intraoral structure. The method further includes providing the first frequency and the second frequency to the at least one electrode to generate an electrical field that electrically motivates the active agent suspended in a fluid medium contained in the intraoral delivery tray toward the intraoral structure via dielectrophoresis and providing the third frequency to the at least one electrode to increase the uptake of the active agent into intraoral structure via alternating current electroosmosis.

44 Claims, 27 Drawing Sheets

(51) Int. Cl.
*A61N 1/05* (2006.01)
*A61N 1/32* (2006.01)
*A61C 8/02* (2006.01)

(56) References Cited

U.S. PATENT DOCUMENTS

| | | | |
|---|---|---|---|
| 6,382,979 B2* | 5/2002 | Lindquist | 433/215 |
| 6,749,427 B1* | 6/2004 | Bretscher et al. | 433/30 |
| 8,956,157 B2* | 2/2015 | Rutberg et al. | 433/32 |
| 2001/0038998 A1* | 11/2001 | Lindquist | 433/215 |
| 2005/0273046 A1* | 12/2005 | Kwiatkowski | A61K 9/0009 604/20 |
| 2008/0146986 A1 | 6/2008 | Riga et al. | |
| 2008/0280260 A1* | 11/2008 | Belikov et al. | 433/215 |
| 2009/0117513 A1* | 5/2009 | Nemeh et al. | 433/32 |
| 2010/0137780 A1 | 6/2010 | Singh et al. | |
| 2012/0156648 A1 | 6/2012 | Kaufman et al. | |
| 2012/0295218 A1* | 11/2012 | Moll | 433/32 |
| 2012/0315596 A1* | 12/2012 | Gan et al. | 433/32 |
| 2014/0093836 A1* | 4/2014 | Wolpo | 433/32 |
| 2014/0162206 A1* | 6/2014 | Ivanoff et al. | 433/32 |
| 2015/0072300 A1* | 3/2015 | Wolpo | 433/27 |

OTHER PUBLICATIONS

Ivanoff et al., "Dielectrophoresis: A model to transport to transport drugs directly into teeth," Electrophoresis. vol. 33, No. 8 pp. 1311-1321 (2012).

Ivanoff et al., "Dielectrophoretic transport of fluoride into enamel," Am. J. Dent. vol. 24, No. 6 pp. 341-345 (2011).

Ivanoff et al., "Microhardness recovery of demineralized enamel after treatment with fluoride gel or CPP-ACP paste applied topically or with dielectrophoresis," Am. J. Dent. vol. 25, No. 2 pp. 109-113 (2012).

Luo et al., "Nanoelectrode arrays for on-chip manipulation of biomolecules in aqueous solutions," Microelectronic Engineering. vol. 83 pp. 1634-1637 (2006).

Ivanoff, "Dielectrophoretic Transport Increases Depth of Penetration of Fluoride into Enamel," (1 page).

Ivanoff et al. "Enhanced penetration of fluoride particles into bovine enamel by combining dielectrophoresis with AC electroosmosis" *Electrophoresis*, vol. 34 (20-21 pp. 2945-2955 (2013).

Ivanoff et al., "Fluoride uptake by human tooth enamel: Topical application versus combined dielectrophoresis and AC electroosmosis," Am. J. Dent. vol. 26(3), 166-172 (13 pages) (2013).

Ivanoff et al. "19th International Symposium, Exhibit & Workshops on Electro- and Liquid, Phase-separation Technique, ITP 2012 Book of Abstracts (all Lecture and Poster Presentations)" L-143 Dielectrophoretic Drug Transport into Teeth. [abstract].

Burke, "Nanodielectrophoresis: Electronic nanotweezers," Nalwa, H.S. (Ed.), Encyclopedia of Nanoscience and Nanotechnology. American Scientific: Stevenson Ranch, California, USA. vol. 6 pp. 623-641 (2004).

Castellanos et al., "Electrohydrodynamics and dielectrophoresis in microsystems: Scaling laws," J. Phys. D: Appl. Phys. vol. 36, No. 20 pp. 2584-2597(2003).

Chaurey et al., "Scaling down constriction-based (electrodeless) dielectrophoresis devicesfor trapping nanoscale bioparticles in physiological media of high-conductivity," Electrophoresis vol. 34, No. 7 pp. 1097-1104 (2013).

Chaurey et al.,"Floating-electrode enhanced constriction dielectrophoresis for biomolecular trapping in physiological media of high conductivity," Biomicrofluidics. vol. 6, No. 1 p. 012806 (2012).

Erickson et al., "Analysis of alternating current electroosmotic flows in a rectangular microchannel," Langmuir vol. 19 pp. 5421-5430 (2003).

Gascoyne et al., "Particle Separation by Dielectrophoresis," Electrophoresis vol. 23 pp. 1973-1983 (2002).

Gonzalez et al., "Fluid flow induced by non-uniform ac electric fields in electrolytes on microelectrodes. II. A linear double-layer analysis," Phys. Rev. E. vol. 61, No. 4, pp. 4019-4028 (2000).

Green et al., "Fluid flow induced by nonuniform ac electric fields in electrolytes on microelectrodes. I. Experimental measurements," Phys. Rev. E. vol. 61, No. 4 pp. 4011-4018 (2000).

Green et al., "Fluid flow induced by nonuniform ac electric fields in electrolytes on microelectrodes. III. Observation of streamlines and numerical simulation," Phys. Rev. E vol. 66, No. 2:026305 (2002).

Green, N.G., and Morgan, H., "Dielectrophoretic separation of nanoparticles," J. Phys. D: Appl. Phys. vol. 30, No. 11 pp. L41-L44 (1997).

Green, N.G., and Morgan, H., "Separation of submicrometre particles using a combination of dielectrophoretic and electrohydrodynamic forces," J. Phys. D: Appl. Phys. vol. 31 pp. L25-30 (1998).

Hasan, R.S.M., and Khurma, A., "AC dielectrophoresis using elliptic electrode geometry," Journal of Sensors. Article ID 204767 (8 pages) (2011).

Holmes et al., "Cell positioning and sorting using dielectrophoresis," European Cells and Materials vol. 4, No. 2 pp. 120-122 (2002).

Hughes, et al., "Dielectrophoretic trapping of single sub-micrometre scale bioparticles," J. Phys. D, vol. 31 pp. 2205-2210 (1998).

Islam et al., "Enhancing microcantilever capability with integrated AC electroosmosis trapping," Microfluid. Nanofluid. vol. 3, No. 3 pp. 269-375 (2007).

Ivanoff et al., "Dielectrophoretic Drug Transport into Teeth," in 19th International Symposium, Exhibit & Workshops on Electro- and Liquid, Phase-separation Technique, ITP 2012 Book of Abstracts, Abstract L-143.

Ivanoff et al. "Enhanced penetration of fluoride particles into bovine enamel by combining dielectrophoresis with AC electroosmosis" Electrophoresis, vol. 34 (20-21 pp. 2945-2955 (2013); DOI:10.1002/elps.201300206.

Ivanoff et al., "Breaking the fluoride diffusion barrier with combined dielectrophoresis and AC electroosmosis," American Journal of Dentistry. vol. 26, No. 4, pp. 228-236 (2013).

Ivanoff et al., "Fluoride uptake by human tooth enamel: Topical application versus combined dielectrophoresis and AC electroosmosis," Am. J. Dent. vol. 26(3), 166-172 (2013).

Ivanoff, "Dielectrophoretic Transport Increases Depth of Penetration of Fluoride into Enamel," In Effectvie Community Preventitive Programs: American Public Health Association 140th Annual Meeting & Expo, San Francisco, California, Oct. 27-Oct. 31, 2012; abstract 259087.

Iverson et al., "Recent advances in microscale pumping technologies: a review and evaluation," International Journal of Microfluidics and Nanofluidics vol. 5, Issue 2 pp. 145-174 (2008).

Khoshmanesh et al., "Dielectrophoretic platforms for bio-microfluidic systems," Biosens. Bioelectron. vol. 26, No. 5 pp. 1800-1814 (2011).

Lian, M., and Wu, J., "Ultrafast micropumping by biased alternating current electrokinetics," Appl. Phys. Lett. vol. 94 p. 064101 (2009).

Liao et al., Nano-constriction device for rapid protein preconcentration in physiological media through a balance of electrokinetic forces Electrophoresis. vol. 33 pp. 1958-1966 (2012).

Liu et al., "Microfluidic Pumping based on Traveling-Wave Dielectrophoresis," Nanoscale and Microscale Thermophysical Engineering. vol. 13 pp. 109-133 (2009).

Melvin et al., "On-chip collection of particles and cells by AC electroosmotic pumping and dielectrophoresis using asymmetric electrodes," Biomicrofluidics. vol. 5 p. 034113 (2011).

Morgan et al., "Separation of submicron bioparticles by dielectrophoresis," Biophys. J. vol. 77, No. 1 pp. 516-525 (1999).

Pethig, "Review article-dielectrophoresis: status of the theory, technology, and applications," Biomicrofluidics. vol. 4, No. 2 pp. 1-35 (2010).

Ramos et al., "A linear analysis of the effect of Faradaic currents on travelling-wave electroosmosis," J. Colloid Inderface Sci. vol. 309, No. 2 pp. 323-331 (2007).

Ramos et al., "AC electric-field-induced fluid flow in microelectrodes," J. Colloid Interface Sci. vol. 217 pp. 420- 422 (1999).

(56) References Cited

OTHER PUBLICATIONS

Ramos et al., "AC electrokinetics: a review of forces in microelectrode structures," J. Phys. D: Appl. Phys. vol. 31 pp. 2338-2353 (1998).

Ramos et al., "Pumping of liquids with ac voltages applied to asymmetric pairs of microelectrodes," Phys. Rev. E. vol. 67 p. 056302 (2003).

Singal et al., "A novel valveless micropump with electrohydrodynamic enhancement for high heat flux cooling," IEEE Trans. Advanced Packaging vol. 28 pp. 216-230 (2005).

Urbanski et al., "Fast ac electro-osmotic micropumps with nonplanar electrodes," Appl. Phys. Lett. vol. 89, No. 14:143508 (2006).

Wong et al., "Electrokinetic bioprocessor for concentrating cells and molecules," Anal. Chem. vol. 76, No. 23 pp. 6908-6914 (2004).

Wu et al., "Long-range AC electrokinetic trapping and detection of bioparticles," Industr. Eng. Chem. Research. vol. 44, No. 8 pp. 2815-2822 (2005).

Wu et al., "Transport of particles and microorganisms in microfluidicchannels using rectified ac electro-osmotic flow," Biomicrofluidics, vol. 5:013407 (2011).

Wu, J., "Biased ac electro-osmosis for on chip bioparticle processing," IEEE Trans. Nanotechnol. vol. 5, No. 2 pp. 84-88 (2006).

Wu, J., "Interaction of electrical fields with fluids: laboratory-on-chip applications," IET Nanobiotechnol. vol. 2, No. 1 pp. 14-27 (2008).

Zeng et al., "Fabrication and characterization of electroosmotic micropumps," Sensor and Actuator B vol. 79 pp. 107-114 (2001).

Zhang et al., "Simulation of ion generation and breakdown in atmospheric air," J. Applied Physics vol. 96 pp. 6066-6072 (2004).

"Comsol" supporting information for Ivanoff et al. Electrophoreses, 34 (20-21) 2945-2955 (2013). Available online at onlinelibrary.wiley.com/doi/10.1002/elps.201300206/suppinfo.

Pohl, "The motion and precipitation of suspensoids in divergent electric fields," J. Appl. Phys. vol. 22 pp. 869-871 (1951).

Pohl., "Some effects of nonuniform fields on dielectrics," J. Appl. Phys., vol. 29, No. 8 pp. 1182-1188 (1958).

Suehiro et al., "The dielectrophoretic movement and positioning of a biological cell using three-dimensional grid electrode system," J. Physics D vol. 31 pp. 3298-3305 (1998).

Wu, J., and Chang, H.C., "Asymmetrically biased AC electrochemical micropump," AIChE Annual Meeting. Austin, Texas (Nov. 7-12, 2004).

* cited by examiner

TABLE 2. CALCULATED DEP FORCES (N) FOR 5V EXCITATION

| PROBING POINT MEASURED RELATIVE TO CORNER OF TOP ELECTRODE ASSEMBLY | COPLANAR EXCITATION | | CROSS-PLANAR EXCITATION | |
|---|---|---|---|---|
| | f = 10 Hz | f = 5 kHz | f = 10 Hz | f = 5 kHz |
| VERTICALLY 1 μm AWAY | -9.190x10⁻¹² | 9.586x10⁻¹⁰ | -4.103x10⁻¹² | 4.279x10⁻¹⁰ |
| VERTICALLY 5 μm AWAY | -8.123x10⁻¹³ | 8.473x10⁻¹¹ | -9.026x10⁻¹³ | 9.415x10⁻¹¹ |
| VERTICALLY 100 μm AWAY | -4.513x10⁻¹⁵ | 4.707x10⁻¹³ | -9.846x10⁻¹⁵ | 1.027x10⁻¹² |
| HORIZONTALLY 1 μM AWAY | -1.142x10⁻¹¹ | 1.191x10⁻⁹ | -4.308x10⁻¹² | 4.493x10⁻¹⁰ |
| HORIZONTALLY 5 μM AWAY | -1.083x10⁻¹² | 1.130x10⁻¹⁰ | -2.002x10⁻¹² | 2.088x10⁻¹⁰ |
| HORIZONTALLY 100 μM AWAY | -6.203x10⁻¹⁵ | 6.471x10⁻¹³ | -1.805x10⁻¹⁴ | 1.883x10⁻¹² |

FIG. 4J

METHODS AND SYSTEMS COMBINING AC ELECTROOSMOSIS WITH DIELECTROPHORESIS TO ENHANCE DELIVERY OF ACTIVE AGENTS INTO INTRAORAL STRUCTURES

CROSS-REFERENCE TO RELATED APPLICATION

The presently disclosed subject matter claims the benefit of U.S. Provisional Patent Application Ser. No. 61/731,993, filed Nov. 30, 2012, the disclosure of which is incorporated herein by reference in its entirety.

TECHNICAL FIELD

The subject matter described herein relates generally to applying active agents to an intraoral structure. More particularly, the subject matter disclosed herein relates to methods and systems for delivering an active agent to an intraoral structure where such methods and systems are particularly suitable for use, for example and without limitation, for combining alternating current electroosmosis (ACE) with dielectrophoresis (DEP) to enhance delivery into intraoral structures.

BACKGROUND

The use of fluorides is a major factor toward preventing cavities. Maintaining therapeutic levels of fluoride over time and reducing baseline risk is essential to fluoride's efficacy. However, current topical fluoride treatments are readily soluble in saliva, quickly dissolving and exhausting their efficacy within 24 hours. Notwithstanding, a traditional application of 1.23% acidulated phosphate fluoride (APF) gel in a disposable tray can result in fluoride ingestion of between 14 and 31 mg. "One-minute" topical fluoride gels may reduce exposure time and incidence of ingestion. However, most fluoride depositions on sound enamel do not last more than 24 hours. This has been found true in both in vitro and in vivo applications and is attributed to the release of loosely bound fluoride on enamel.

Currently available diffusion methods are inadequate for effectively transporting therapeutic agents deeper than 20 μm into enamel, at least partially due to the fact that enamel has a 100-250 μm thick surface layer with very low permeability. Therefore, there exists a need for more efficient delivery methods and systems to introduce active agents into intraoral structures.

SUMMARY

According to one embodiment, the subject matter described herein can include a method for delivering an active agent into an intraoral structure. The method can include generating an electrical signal that includes a first frequency, a second frequency, and a third frequency, and supplying the electrical signal to an embedded circuit contained in an intraoral delivery tray, where the embedded circuit can include at least one electrode that includes projections positioned proximally to a surface of an intraoral structure. The method can further include providing the first frequency and the second frequency to the at least one electrode to generate an electrical field that electrically motivates the active agent suspended in a fluid medium contained in the intraoral delivery tray toward the intraoral structure via dielectrophoresis, and providing the third frequency to the at least one electrode to increase the uptake of the active agent into intraoral structure via alternating current electroosmosis.

According to another embodiment, the subject matter described herein comprises an intraoral delivery system comprising an intraoral delivery tray including an embedded circuit comprising at least one electrode, where the at least one electrode comprises a portion that includes projections positioned proximally to a surface of an intraoral structure. The system can further include a signal generator module configured to provide an electrical signal to the embedded circuit, wherein the electrical signal includes a first frequency, a second frequency, and a third frequency, where the first frequency and the second frequency can increase molecular availability and mobility of an active agent suspended in a fluid medium contained in the intraoral delivery tray via dielectrophoresis and the third frequency increases the uptake of the active agent by the intraoral structure via alternating current electroosmosis.

According to yet another embodiment, the subject matter described herein comprises a method for delivering an active agent into an intraoral structure. The method can include generating an electrical signal that includes a first frequency, a second frequency, and a third frequency, and supplying the electrical signal to at least one electrode that includes projections positioned proximally to a surface of an intraoral structure. The method can further include providing the first frequency and the second frequency to the at least one electrode to generate an electrical field that electrically motivates the active agent toward the intraoral structure via dielectrophoresis, and providing the third frequency to the at least one electrode to increase the uptake of the active agent into intraoral structure via alternating current electroosmosis.

Accordingly, it is an object of the presently disclosed subject matter to provide methods and systems for enhancing delivery of active agents into intraoral structures.

A certain object of the presently disclosed subject matter having been stated hereinabove, which is addressed in whole or in part by the presently disclosed subject matter, other objects and advantages will become apparent to those of ordinary skill in the art after a study of the following description of the presently disclosed subject matter and in the accompanying non-limiting Figures.

BRIEF DESCRIPTION OF THE DRAWINGS

The subject matter described herein will now be explained with reference to the accompanying drawings, of which:

FIG. 4J are exemplary calculations of DEP forces presented in a table in accordance with embodiments of the subject matter described herein.

DETAILED DESCRIPTION

Figure 1A:
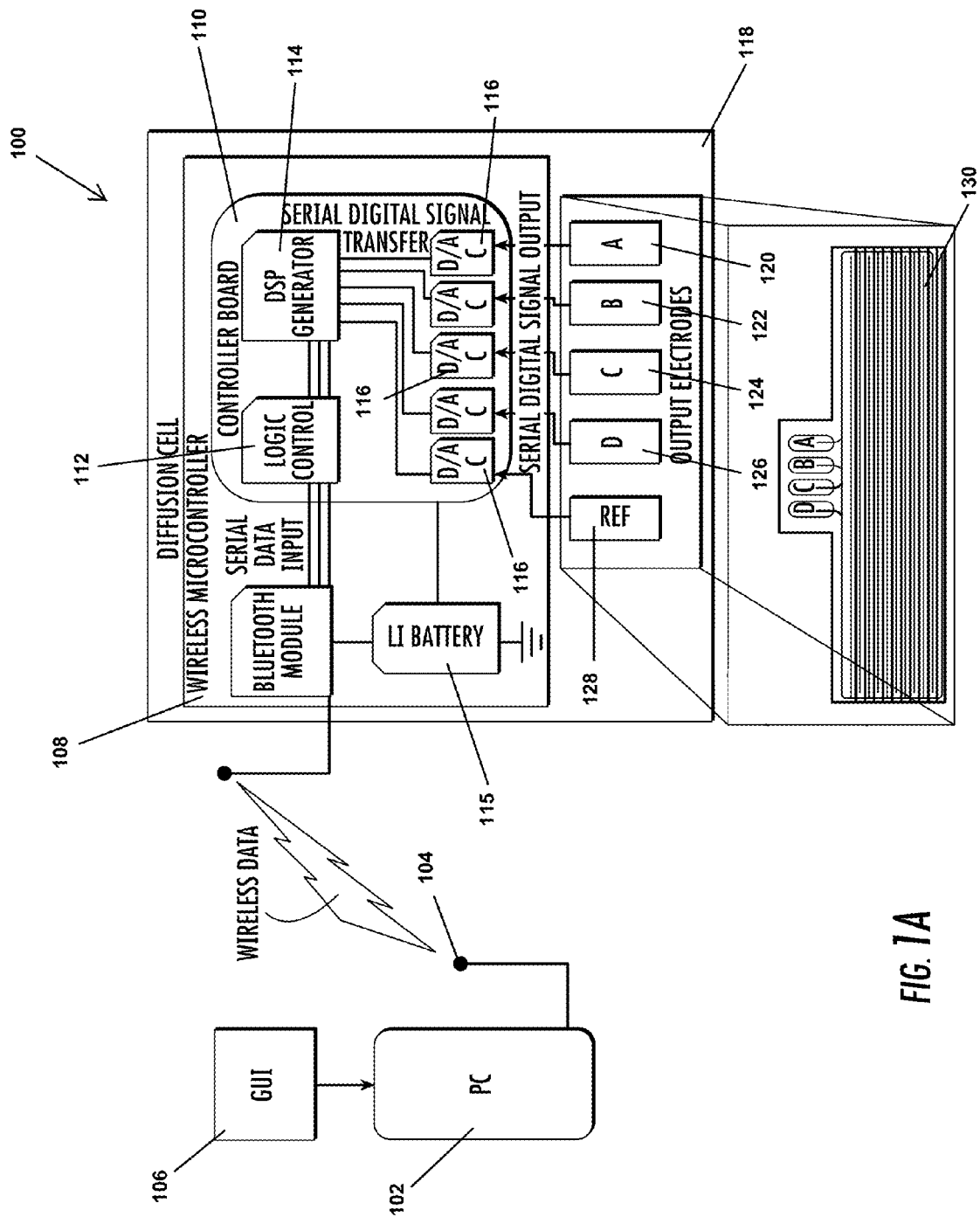
FIG. 1A illustrates an exemplary embodiment of a wireless enabled microcontroller system in accordance with the subject matter disclosed herein.

The presently disclosed subject matter will now be described more fully hereinafter with reference to the accompanying examples, in which representative embodiments are shown. The presently disclosed subject matter can, however, be embodied in different forms and should not be construed as limited to the embodiments set forth herein. Rather, these embodiments are provided so that this disclosure will be thorough and complete, and will fully convey the scope of the embodiments to those skilled in the art.

Unless otherwise defined, all technical and scientific terms used herein have the same meaning as commonly understood by one of ordinary skill in the art to which this presently described subject matter belongs. All publications, patent applications, patents, and other references mentioned herein are incorporated by reference in their entirety.

Following long-standing patent law convention, the terms "a" and "an" mean "one or more" when used in this application, including the claims.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter. Thus, the term "about", as used herein when referring to a value or to an amount of mass, weight, time, temperature, volume, or percentage is meant to encompass variations of ±20% or ±10%, more preferably ±5%, even more preferably ±1%, and still more preferably ±0.1% from the specified amount, as such variations are appropriate to perform the disclosed method.

The term "and/or" when used to describe two or more activities, conditions, or outcomes refers to situations wherein both of the listed conditions are included or wherein only one of the two listed conditions are included.

The term "comprising", which is synonymous with "including," "containing," or "characterized by" is inclusive or open-ended and does not exclude additional, unrecited elements or method steps. "Comprising" is a term of art used in claim language which means that the named elements are essential, but other elements can be added and still form a construct within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed and claimed subject matter can include the use of either of the other two terms.

As used herein, the term "ACEO" is synonymous to "ACE", which both refer to alternating current electroosmosis, the physical phenomenon of using AC potential to move fluids through a porous medium.

The methods and systems disclosed herein can be used on a sample either in vitro (for example, on isolated structures or tissues) or in vivo in a subject (i.e. living organism, such as a patient). In some embodiments, the subject is a human subject, although it is to be understood that the principles of the presently disclosed subject matter indicate that the presently disclosed subject matter is effective with respect to all vertebrate species, including mammals, which are intended to be included in the terms "subject" and "patient". Moreover, a mammal is understood to include any mammalian species for which employing the compositions and methods disclosed herein is desirable, particularly agricultural and domestic mammalian species. More particularly provided are methods and compositions for mammals such as humans, as well as those mammals of importance due to being endangered (such as Siberian tigers), of economic importance (animals raised on farms for consumption by humans), and/or of social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses.

The disclosed subject matter includes methods and systems related to an intraoral drug delivery system that is configured to combine ACE with dielectrophoresis (DEP) to enhance delivery of active agents into tissues (e.g., the delivery of fluoride into human teeth). As described herein, DEP includes the movement of particles under the influence of a nonuniform electrical field. Unlike electrophoresis (EP), in which dispersed charged particles move in a uniform (direct current) electrical field, DEP does not depend on the polarity of the field or the charge of the particles. In contrast, DEP uses the gradient of the non-uniform field and the inherent dielectric properties of particles to generate electromotive forces.

Since the strength of the electromotive force depends on particle and medium properties, as well as on applied electric field frequencies, particles can be selectively manipulated. As a result, DEP can be used to manipulate, transport, separate, and sort particles in a wide array of applications, including separating cells, stretching DNA molecules, and assembling nano-circuits. The effects of DEP can be manipulated to separate fluoride particles from excipient components of fluoride gel to enhance their diffusion into the enamel.

ACE can also has significant potential for administering precisely targeted drugs or other agents through various tissues. Electroosmosis (EO) can be referred to as using DC potential to moving fluids through a porous medium. As with EO, ACEO is also based on the ion migration within a nanometer layer of charges/ions at the interfaces of electrolytes and solids (double layer). This layer of charges can migrate under electric fields tangential to the interface, and because of fluid viscosity, the ion movement carries along its surrounding fluids, leading to fluid motion. In ACEO, the charges in the double layer are induced by AC potentials, and tangential E-fields are also from the same voltage source. Therefore, the changes of polarities in charges and field directions are simultaneous and cancelled out, maintaining steady ion migration and fluid motion. By adjusting the amplitude and frequency of AC signals, a variety of directed surface flows can be produced on electrodes to manipulate and transport particles. In symmetric systems (both spatial and temporal), the resulting liquid flow is alternating in direction with a zero offset. To obtain directionality asymmetry can be added either in space (by electrode geometry) or in time (by applying asymmetric AC signals).

More effective delivery of therapeutic agents into enamel can be useful in dentistry because existing passive or active diffusion methods are inadequate for effectively transporting therapeutic agents deeper than approximately 20-50 μm into enamel. Similarly, the transport of agents via DEP-enhanced diffusion is only effective up to 50 μm as well. Permeability studies have shown that enamel has a 100-250 μm thick surface layer with very low permeability. However, by applying an AC electrokinetic force after selectively polarizing and motivating particles with DEP, DEP/ACE can be an effective technique to overcome this surface barrier.

In some embodiments, delivery of fluoride by a DEP technique at 10 Hz and 5000 Hz combined with the application of 400 Hz frequency can significantly increase fluoride uptake and remineralization in tooth enamel. For example, by using a pair of parallel interdigitated array electrodes (IDEs) at three optimal frequencies to manipulate fluoride particles, fluoride uptake can be enhanced to overcome the shortfalls of diffusion.

FIG. 1A illustrates an exemplary embodiment of a wireless enabled microcontroller system, generally designated 100, in accordance with the subject matter disclosed herein. As shown in FIG. 1A, microcontroller system 100 can include a user personal computer (PC) 102 containing a Bluetooth Transceiver 104. PC 102 can be programmed using a graphical user interface (GUI) 106 to communicate to a wireless controller 108 within microcontroller system 100. In some embodiments, wireless microcontroller 108 can be fabricated on a flexible substrate and by way of example and not limitation can span one inch by 1.5 inch in size. Furthermore, wireless microcontroller 108 can include a controller board 110 comprising a logic control system 112 to convert an input from GUI 106 to an output signal to a digital signal processing (DSP) generator 114, and also be powered through a rechargeable lithium-ion battery 115. DSP generator 114 can output a discrete sampled signal, which after passing through a digital-to-analog converter 116 can generate a respective analog signal. There can be some variations in the discrete sampled signal, as dictated by the logic control system, which results in analog signals with temporal variations in voltage amplitude and frequency output to multiple channels. For example, an electrical signal can be generated to include three different frequencies. A standard connector system can be utilized to interface the microcontroller to a diffusion cell 118. In some aspects, the microcontroller system can be modified to include data output to GUI 106 for feedback and monitoring needs.

Furthermore, controller board 110 can be electrically coupled to IDE electrodes for providing AC signals (e.g. the electrical signal generated by the DSP generator) at various frequencies. In some embodiments, the AC signals can be sinusoidal, square, triangular, or pulse in nature. For example, as illustrated in FIG. 1A, individual digital to analog converters 116 can be connected to output electrodes A through D 120, 122, 124, 126 and a reference electrode 128 to provide AC signals to an IDE electrode array 130. The different frequencies can be applied to IDE electrodes to motivate active agent movements close to and into target tissues or structures, such as tooth enamels. In some embodiments, the IDEs can be part of an circuit embedded or integrated into an intraoral delivery tray, where one or more IDE electrode can be positioned proximally to a surface of an intraoral structure, such as an intraoral mucosal structure, supporting structure (e.g., bone, periodontal ligament, etc.), boney structure (e.g., palate, maxilla, mandible, etc.), and/or soft tissue structure (e.g., tongue, lips, buccal mucosa, etc.). A first and second frequency can be used to stimulate a DEP effect and motivate the active agent to move toward the tissue or structure. A third frequency within the electrical signal can be utilized to stimulate an ACEO effect on the active agent to increase the uptake into the tissue or structure, either alone or in combination with a first or second frequency. In some embodiments, a signal generator module can be configured to provide an electrical signal to the embedded circuit, wherein the electrical signal can include a first frequency, a second frequency, and a third frequency, wherein the first frequency and the second frequency can be modulated to increase availability and mobility of an active agent (such as molecular availability and mobility) suspended in a fluid medium contained in the intraoral delivery tray via dielectrophoresis (DEP) and the third frequency increases the uptake of the active agent by the intraoral structure via alternating current (AC) electroosmosis.

In some embodiments, the first and second frequencies generated by the signal generator module can be modulated to increase particle availability and/or mobility of an active agent suspended in a fluid medium contained in the intraoral delivery tray via dielectrophoresis (DEP) and the third frequency increases the uptake of the active agent by the intraoral structure via alternating current (AC) electroosmosis.

Figure 1B:
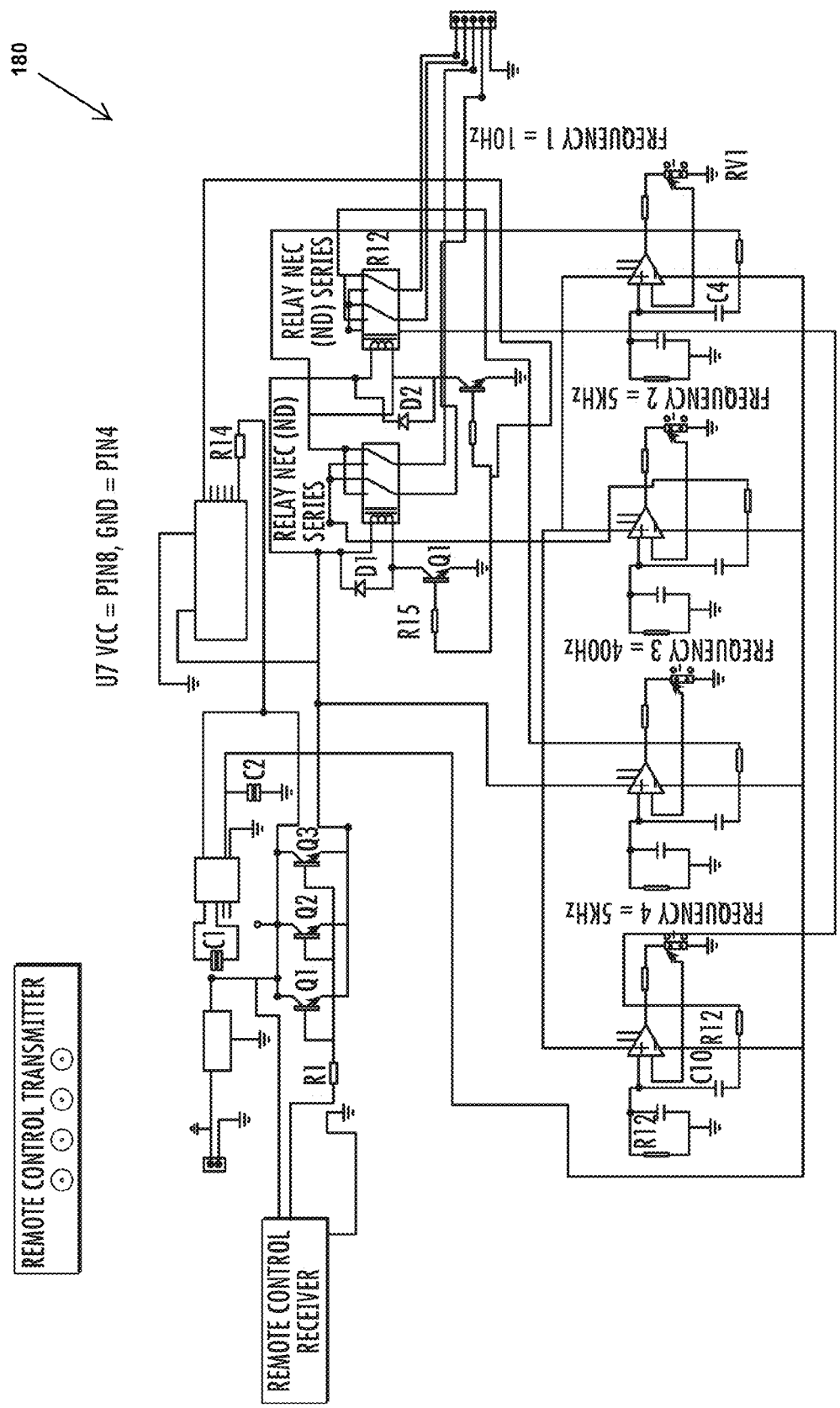
FIG. 1B illustrates an exemplary embodiment of a signal generation circuit in accordance with the subject matter disclosed herein.

FIG. 1B illustrates an exemplary embodiment of a signal generation circuit, generally designated 180, in accordance with the subject matter disclosed herein. Signal generation circuit 180 can be configured to generate 10 Hz and 5000 Hz signals to a distal IDE (shown in FIG. 1C), alternating between the two frequencies every minute, and 5000 Hz and 400 Hz signals to a proximal IDE (shown in FIG. 1C) every minute.

Figure 1C:
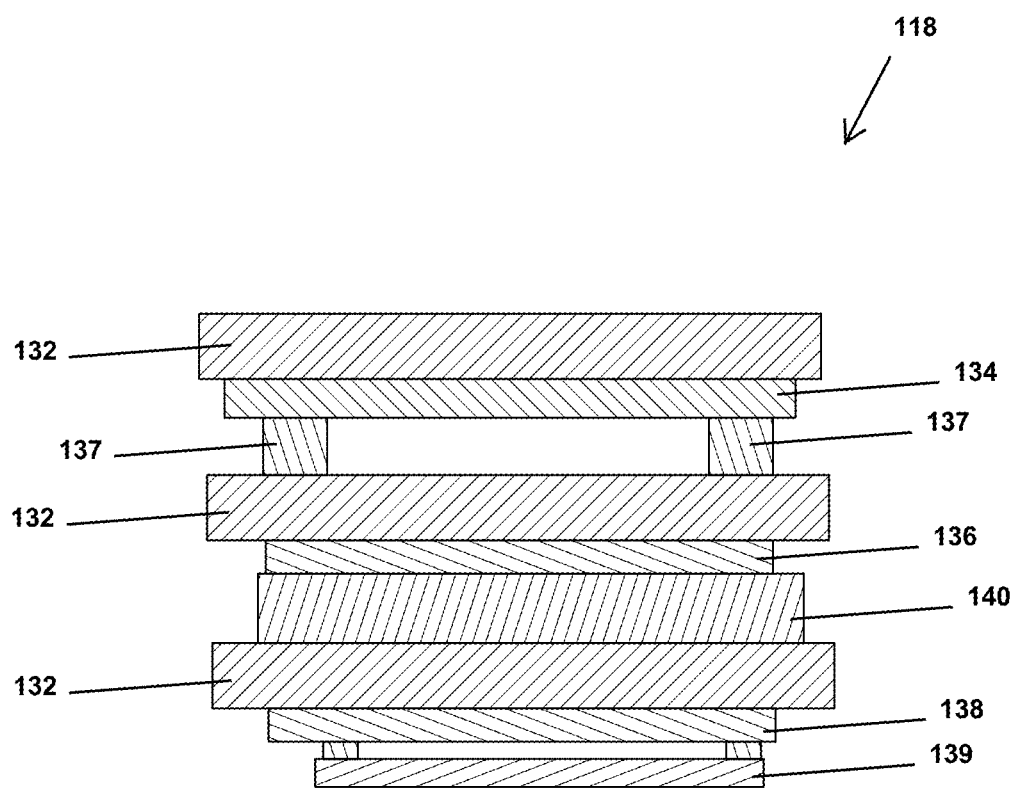
FIG. 1C illustrates an exemplary cross-sectional view of the diffusion cell in accordance with the subject matter disclosed herein.

In some embodiments, diffusion cell 118 can include two IDEs, as illustrated in FIG. 1C. FIG. 1C illustrates an exemplary cross-sectional view of the diffusion cell 118 set up in accordance with the subject matter disclosed herein. As shown in FIG. 1C, diffusion cell 118 can include a reference plate electrode 134, a first IDE array 136, stacked on top of a second IDE array 138, where the second IDE array 138 can come into close contact with the tooth enamel 139. In some embodiments, interdigitated array electrodes 136-138 can be fabricated from flexible printed circuit board material (PCB) 132, each connected to at least one electrical signal generator. A person skilled in the art would recognize that a material, such as a silk-like material or graphene, can be easily utilized to fabricate the IDE electrodes. These materials are mentioned as examples herein to explain the subject matter and are not intended as a limitation.

The component electrodes of each IDE 136-138 can be arranged in a coplanar manner where fingers (i.e., finger projections or projections) from one component electrode interweave with a complimentary electrode, forming interstitial areas between the fingers. Component electrodes can each have an electrical connector that allows for connectivity to an electrical signal source. The interdigitated fingers can be separated, providing sufficient passage to allow active agents, such as active agent particles, to pass through. Furthermore, reference plate electrode 134 can include a non-uniform plate electrode such as but not limited to a copper plate, having representative dimensions (30 mm×40 mm×20 µm), separated by a rubber spacer RS 137 from planar interdigitated array electrodes 136-138, as illustrated in FIG. 1B. All the electrically-conductive components can be independent to each other, separated by an insulator 140, such as a polyimide insulator, and biased against one another to ensure proper electrical transmission.

Figure 1D:
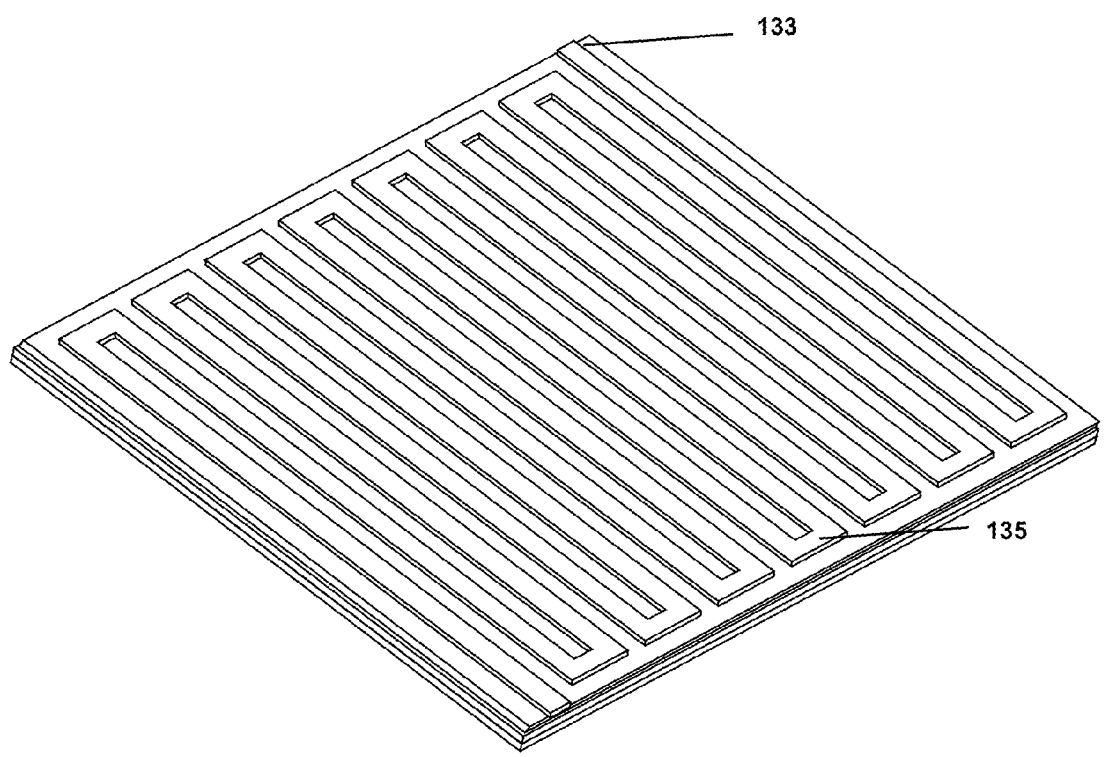
FIGS. 1D to 1I illustrate exemplary embodiments of interdigitated array electrode configurations in accordance with the subject matter disclosed herein.

In some embodiments, as shown in FIG. 1D, the diffusion cell can include two interlaced IDE arrays. As illustrated in FIG. 1D, a second IDE array 135 can be stacked on top of the first IDE 133 and separated by the thickness of the polyimide flexible circuit board substrate—50 µm. IDE array 135 as shown in FIG. 1D can include finger projections that are castellated perpendicular both offset and non-offset to the microelectrodes. The gap between the arrays can be configured to reduce electrical leakage between electrodes, to alleviate electrothermal effects caused by Joule heating, and allow a passage for active agent flow. A layer, which can comprise 500 nm thick parylene C polyimide as a representative non-limiting dimension and material, can be deposited over the electrode array to avoid electrolysis and corrosion of the electrodes when the device is in contact with particle suspensions. Indeed, the layer can comprise any material that facilitates these goals, and/or otherwise enhances the biocompatibility of the electrodes/arrays.

In some embodiments, diffusion cell 118 can include two IDE electrodes, where at least one electrode includes a first electrode and a second electrode aligned in parallel, where the first electrode is supplied with an electrical signal at a first frequency, and the second electrode is supplied with an electrical signal at the first or second frequency, and a third frequency. Furthermore, at least one of the first electrode and the second electrode can include an interdigitated array electrode, complementary IDE component, a portion of an IDE, or any geometric variation sufficient to induce a non-uniform field. In addition, the second electrode can include castellated finger projections positioned proximally to the surface of the intraoral structure.

In some embodiments, diffusion cell 118 can include three IDE electrodes, where the at least one electrode can include a first electrode, a second electrode and a third electrode aligned in parallel, where the first electrode can be supplied with an electrical signal at a first frequency, the second electrode is supplied with the electrical signal at a first or second frequency, and the third electrode can be supplied with an electrical signal at a third frequency. Furthermore, at least one of the first electrode, the second electrode, and the third electrode can include an interdigitated array electrode, complementary IDE component, a portion of an IDE, or any geometric variation sufficient to induce a non-uniform field. In addition, the third electrode can include castellated finger projections positioned proximally to the surface of the intraoral structure.

Figure 1E:
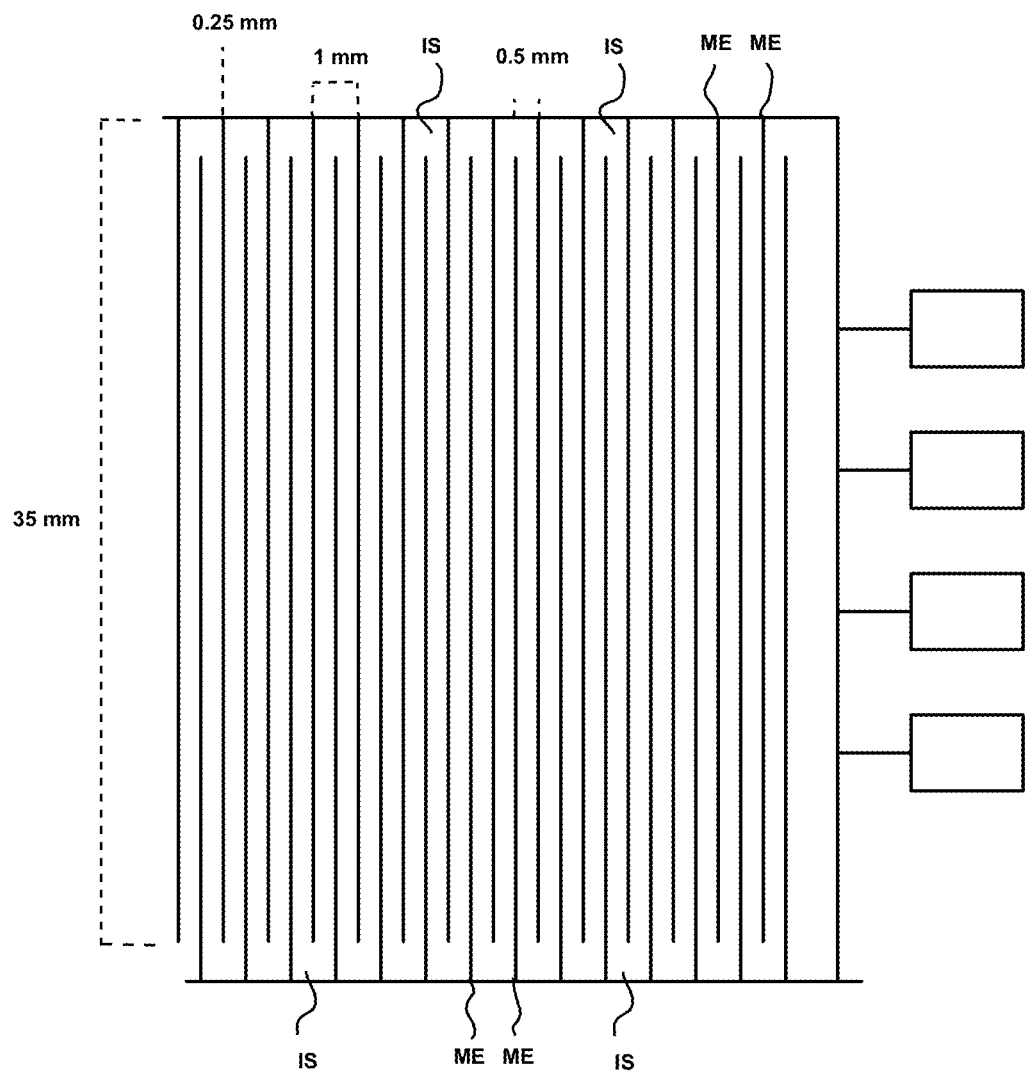
Figure 1F:
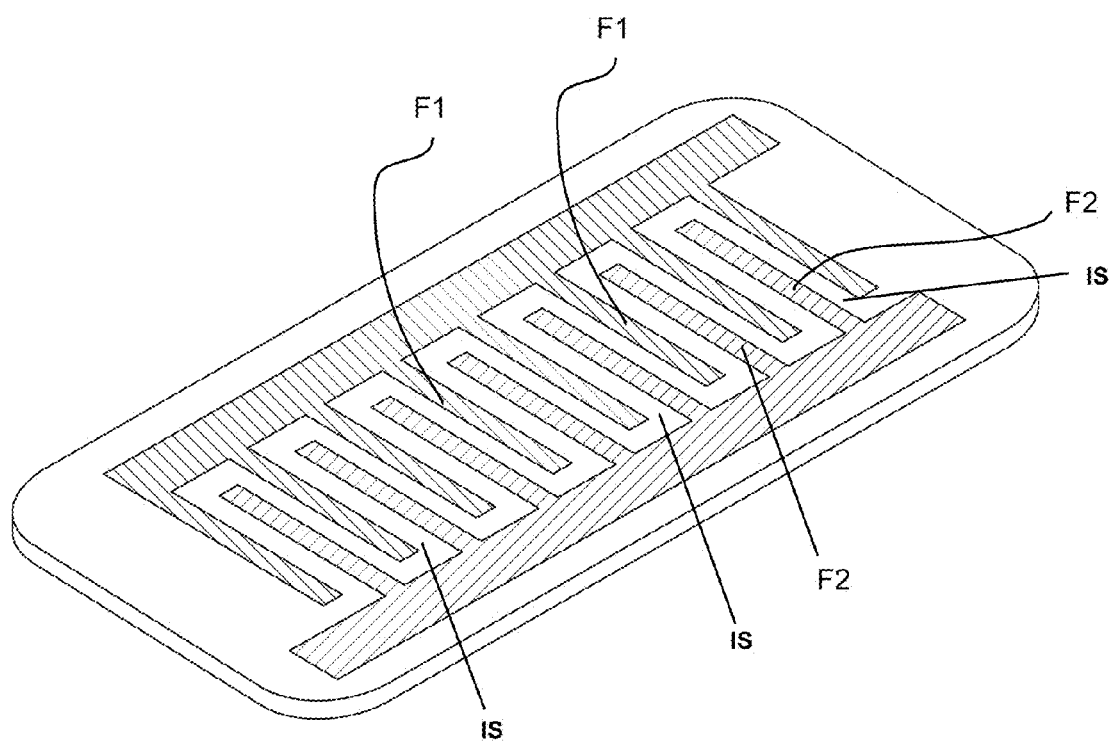

In some embodiments, as shown in FIGS. 1E and 1F, an IDE array 136 can contain 14 pairs of parallel finger microelectrodes ME, each 35 mm long, 250 µm wide, and 30 µm thick, by way of example and not limitation. By way of further example and not limitation, the IDE array can be made out of gold (Au) (or other suitable conductor) and micro-fabricated on flexible printed circuit board (PCB) material, and the IDE's fingers can be separated by intervals of 1 mm containing interstitial spaces IS, which can be 0.5 mm wide, as a representative, non-limiting dimension, and can be planar or castellated in shape. The interdigit gaps IS can reduce electrical leakage between electrodes and allow a passage for active flow. Furthermore, a coating, such as but not limited to a polyimide coating (e.g. thickness 500 nm), can prevent electrolysis and corrosion of the electrodes when the device is in contact with the particle suspensions. Indeed, the coating can comprise any material that facilitate these goals, and/or otherwise enhances the biocompatibility of the electrodes/arrays. The flexible nature of the electrodes disclosed herein can be advantageous to applications such as intraoral use, which can make this electrode design favorable to dentistry uses, among other uses.

Figure 1G:
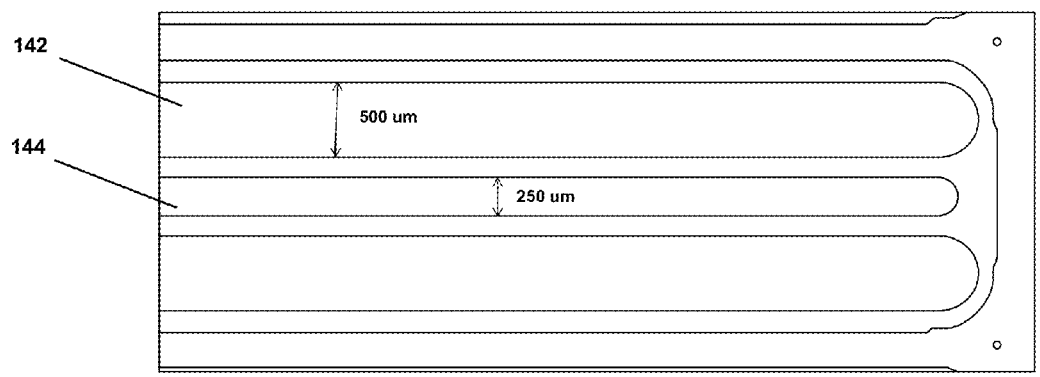
Figure 1H:
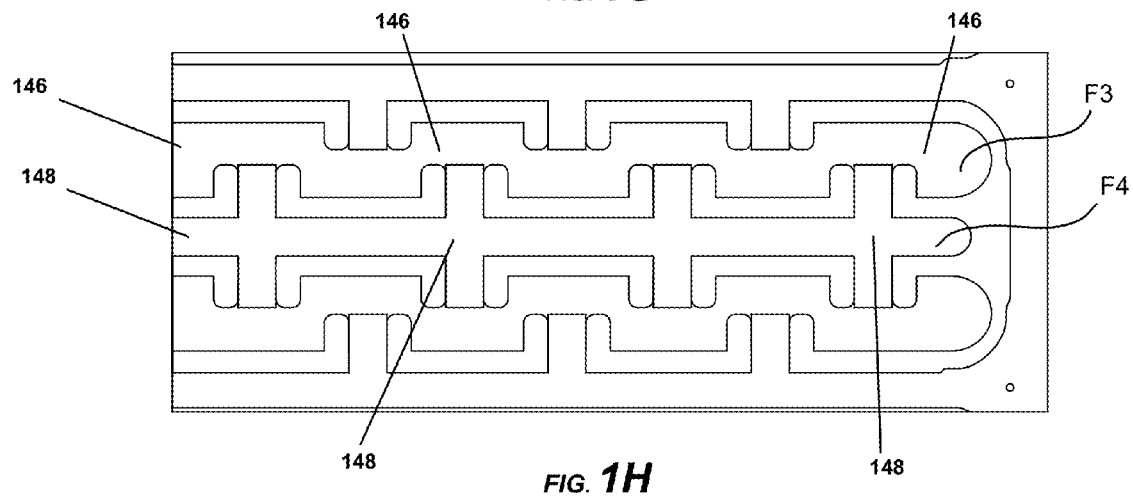

Alternatively, the fingers of the IDEs can have dimensions and geometrical configurations different from the ones presented in FIG. 1E. For example, as illustrated in FIG. 1F, fingers F1 of one IDE component (e.g. 350 µm) can be wider in dimension than fingers F2 of its counter electrode (e.g. 250 µm). In some embodiments, as illustrated in FIG. 1G, fingers 144 of one IDE component (e.g., 250 µm) can be narrower in dimension than the interstitial gaps 142 (e.g., 500 µm) between the fingers 144. Furthermore, as illustrated in FIG. 1H, fingers F3 of a first IDE 146 can be conformed to surfaces with a wave-like, concave, or convex contours. FIG. 1H further illustrates that fingers F4 of a second IDE 148 can have a cross-like repeating pattern and where the protruding castellated part of the cross can interlace with the concave part of the first IDE's finger 146.

Figure 1I:
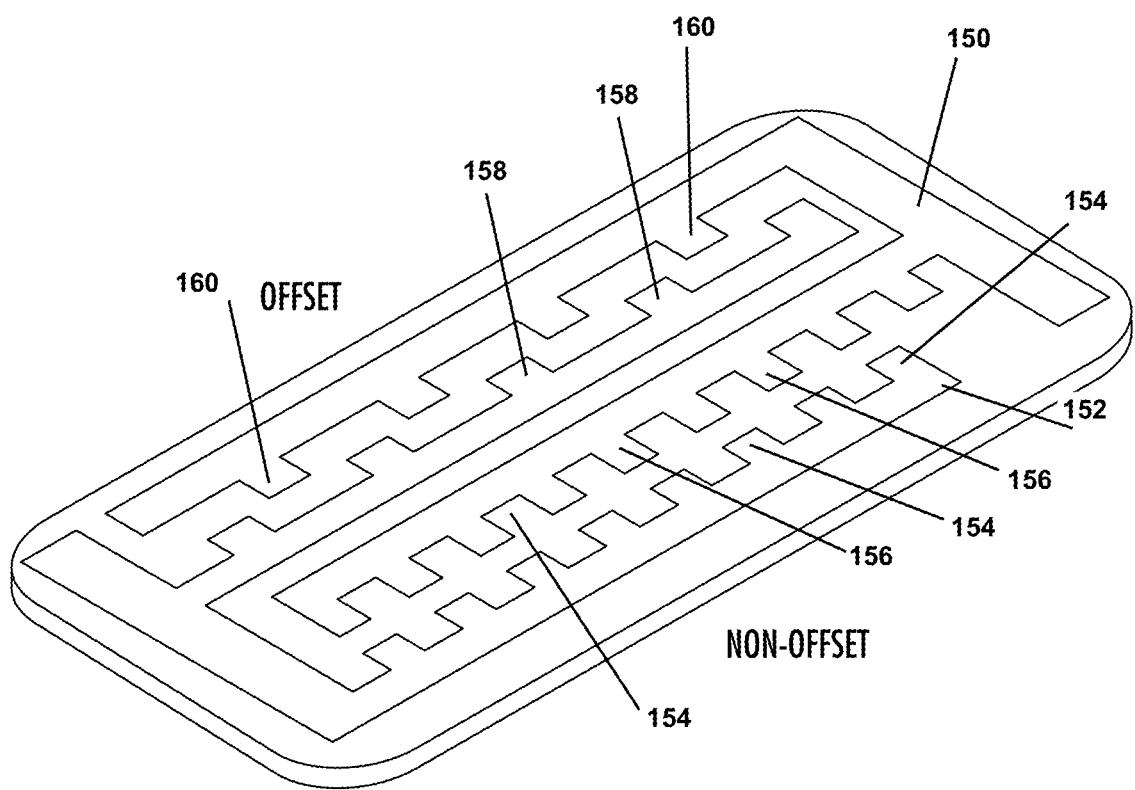

In some embodiments, as illustrated in FIG. 1I, each of IDE fingers 150-152 can be castellated 154-160, and the castellations 154-160 can be configured to either i) be directly facing each other or ii) be interlaced with each other.

Figure 1J:
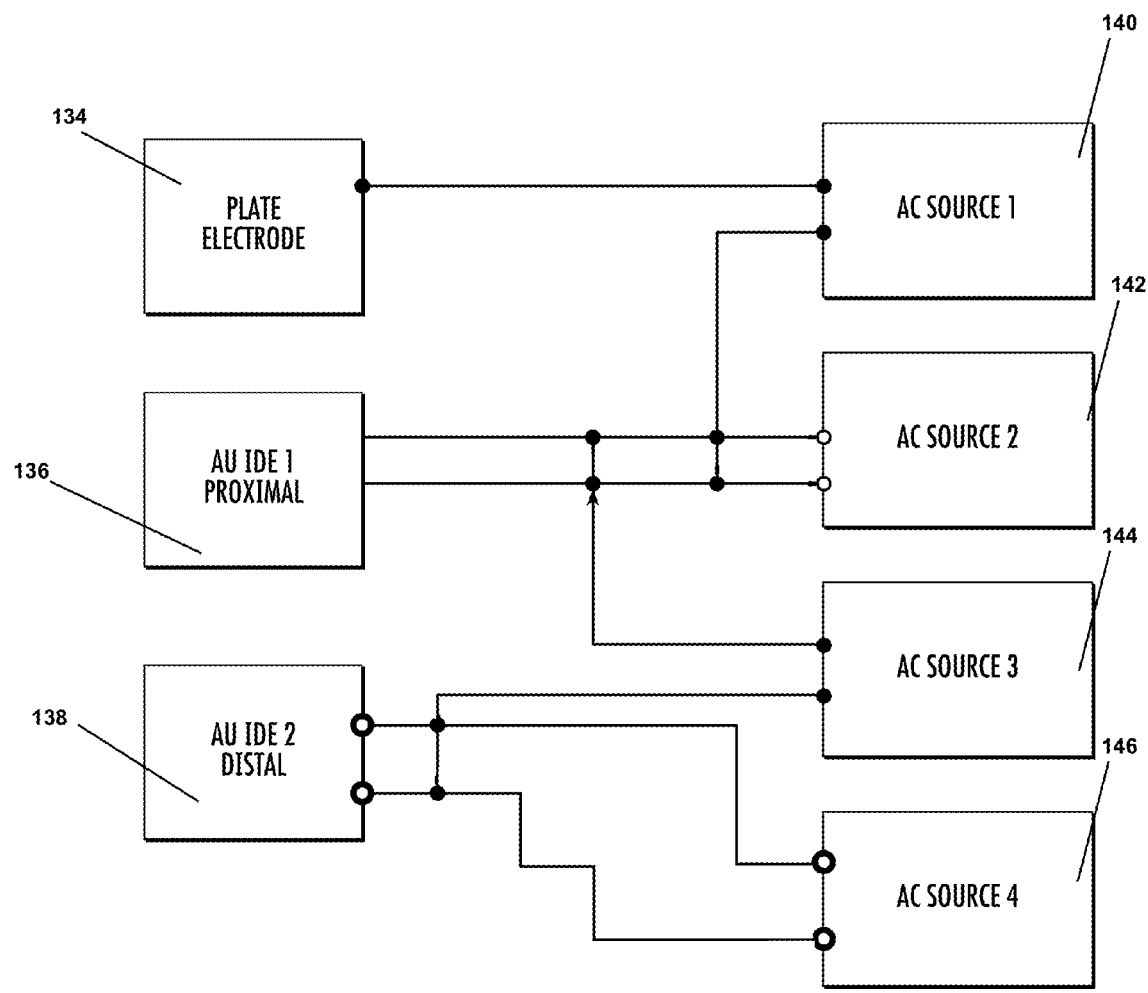
FIG. 1J illustrates a schematic illustration of a biasing circuit for the interdigitated array electrodes in accordance with the subject matter disclosed herein.

In some embodiments, reference plate electrode 134, first IDE array 136, and second IDE array 138 can be biased by four AC power sources as illustrated in FIG. 1J. As shown in FIG. 1J, each of AC power sources 140, 142, 144, 146 includes two terminals, wherein each terminal is capable of providing a signal. AC power source 1 140 can be configured to apply an electrical signal to the reference electrode 134 and the first IDE array 136; AC power source 2 142 can be configured to apply a signal to the component electrodes of the first IDE array 136; AC power source 3 144 can be configured to apply a signal to the first and second IDE array 136-138; and AC power source 4 146 can apply a signal to the component electrodes of the second IDE array 138. As such, AC signals can be applied selectively to either the first IDE 136 or second IDE 138 to establish a field between component electrodes or between both IDE electrodes. Furthermore, the component electrodes of both IDEs 136-138 may be shorted, allowing each IDE to function as a single electrode. The AC signals can be supplied to AC power sources 1-4 140-146 in a successive manner by alternating between two frequencies at each component electrode at one minute intervals. In some embodiments, the current generated can be approximately 0.01-0.03 mA, and the applied sinusoidal field can be approximately 1-5 Vpp/mm. The electric field can be calculated based on a distance for co-planar electrodes of 1 mm (e.g., space between two electrodes of an IDE) and a distance for cross-planar electrodes of 50 μm (e.g., thickness of PCB material).

Figure 2A:
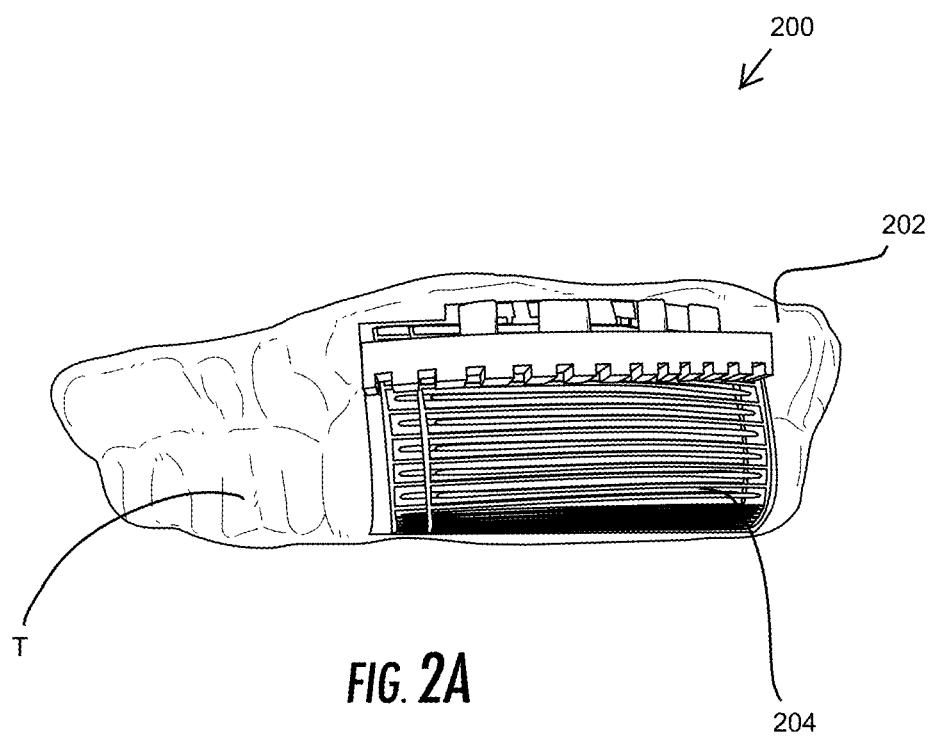
FIG. 2A is an exemplary embodiment of the interdigitated array electrode integrated into an oral tray in accordance with the subject matter disclosed herein.
Figure 2B:
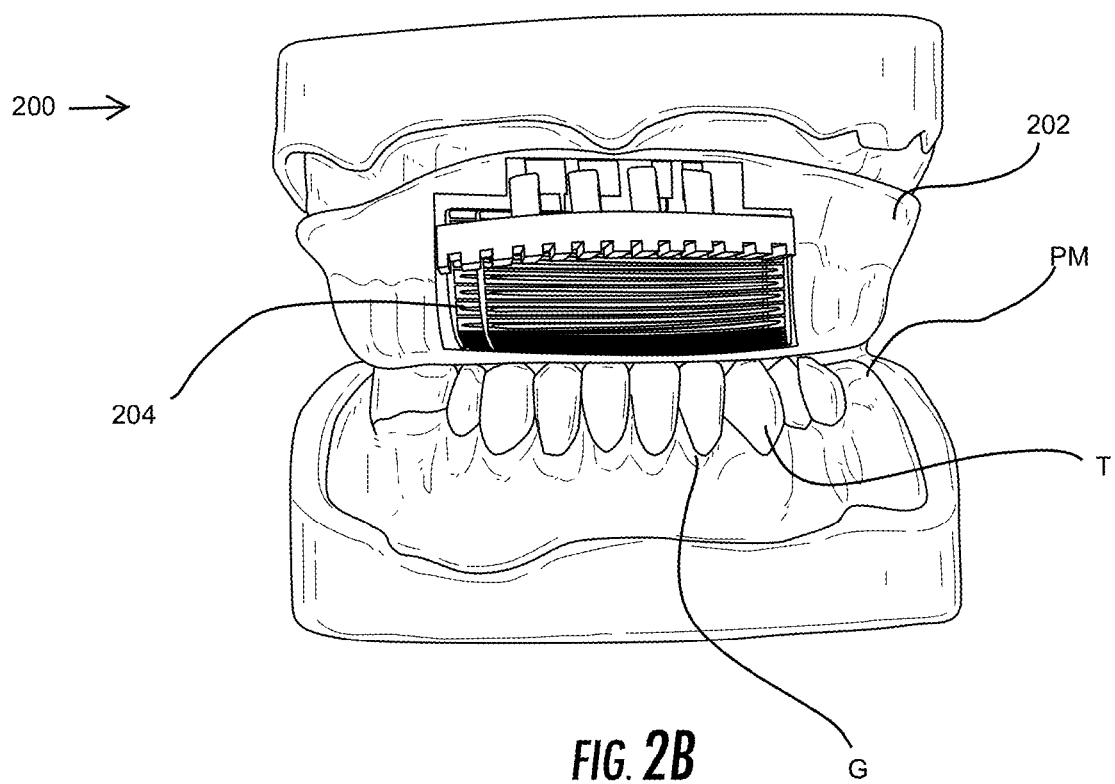
FIGS. 2B and 2C are exemplary embodiments of the oral tray being fitted with human teeth in accordance with the subject matter disclosed herein.
Figure 2C:
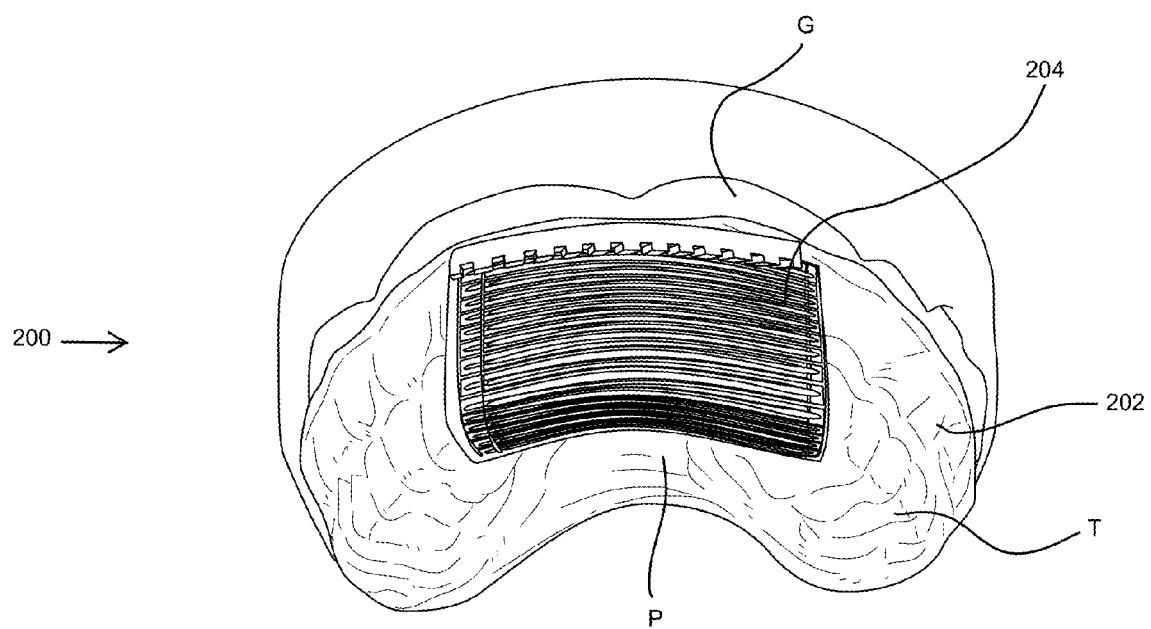
Figure 2D:
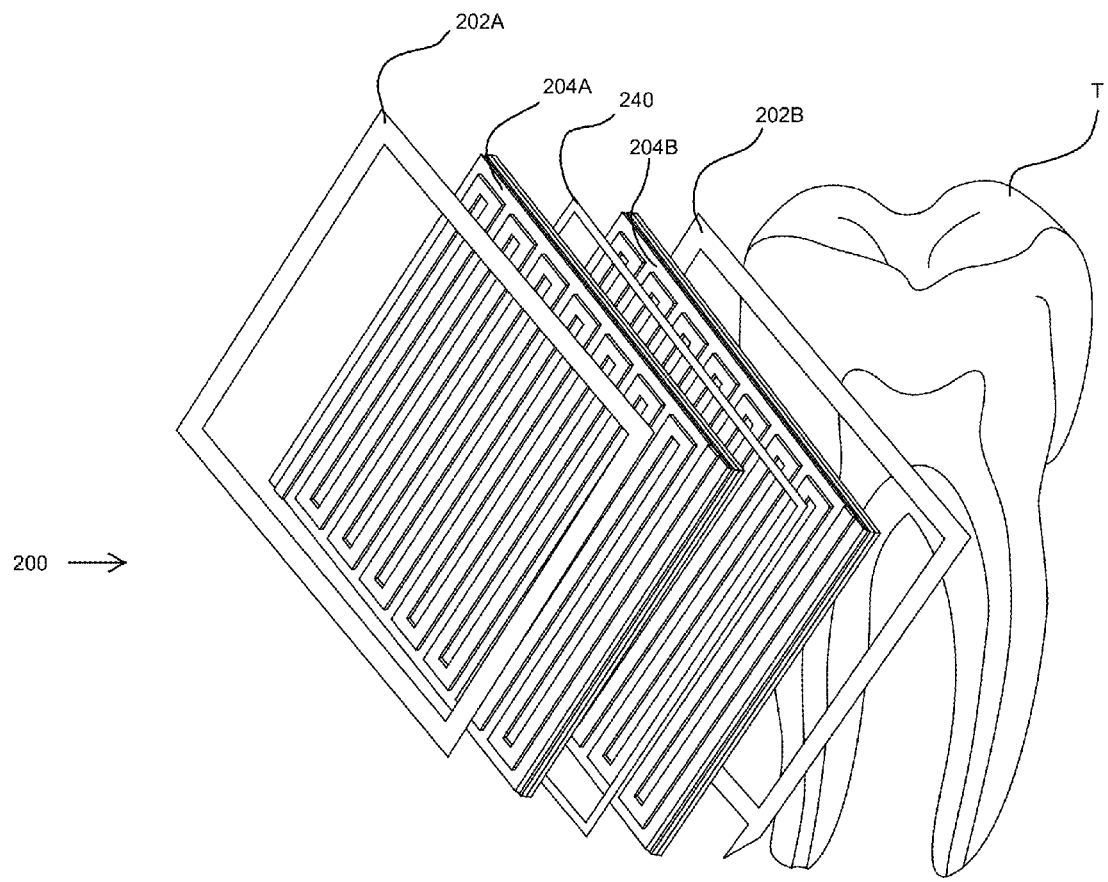
FIG. 2D is an exemplary illustration of the interdigitated array electrodes coming into close proximity of a tooth in accordance with the subject matter disclosed herein.

In some embodiments, the IDE arrays and/or their control circuits can be integrated or embedded into a conventional fluoride tray and applied to human teeth orally, as shown in FIGS. 2A, 2B, 2C, and 2D. In FIG. 2A, the distal IDE arrays 204A and proximal IDE array 204B can be fitted into the inner surface of fluoride tray 202 to provide system 200. Once tray 202 is fitted over a patient's mouth PM, as shown in FIGS. 2B and 2C, IDE arrays 204A 204B can substantially conform to the shape of the teeth T, gingiva G, and/or palate P. As such, when tray 202 is inserted orally, IDE arrays 204 can come into close vicinity or proximity of the tooth's enamel surface (teeth T shown in shadow in FIG. 2A). In FIG. 2D, tray 202 comprises two parts, a polyurethane gel tray 202A component and a fluoride medicament layer component 202B and system 200 further include insulator 240, which can optionally be transparent.

In some embodiments, fluoride particles can be driven through the electrode gaps and into enamel pores by a combination of DEP and ACEO processes. DEP can arise from a difference in electrical permittivity between a particle and the surrounding medium. When a dielectric particle such as a fluoride molecule is suspended in a spatially non-uniform electric field, the applied field can induce a dipole in the particle; the interaction of the induced dipole with the electric field can generates a force. Due to the presence of a field gradient, these forces are not equal and there is a net movement. If the particle is more polarizable than the surrounding medium, the dipole aligns with the field and the force acts up the field gradient towards the region of highest electrical field strength. Conversely, if the particle is less polarizable than the medium, the dipole can align against the field and the particle can be repelled from regions of high electric field. The force is dependent on the induced dipole and is unaffected by the direction of the electric field, responding only to the electric field. Since the alignment of the field is irrelevant, this force can also be generated in AC fields, which can have the advantage of reducing any electrophoretic force (e.g., due to any net particle charge) to zero.

The phenomenon of DEP can occur both in alternating current (AC) and direct current (DC) electric fields and can be applied both to charged and neutral particles. By varying the applied electric field frequency, as well as the type of current (DC or AC), the magnitude and direction of the dielectrophoretic force on the particles can be controlled, thus providing for their manipulation, separation, or orientation.

Active agents including but not limited to drug particles, such as such particles comprising fluoride molecules, can be manipulated by an AC field to enhance drug transport into a target tissue or structure such as tooth enamel because of their dielectric properties. Although the present disclosure describes the use of fluoride molecules, other drug agent particles such as antibiotics, an anesthetic agent, an anti-inflammatory agent, an analgesic, a remineralizing agent, a tooth regenerative agent, a restorative or bonding agent, an immunomodulating agent, a hormone or growth factor, an antimicrobial agent, or a combination thereof can also be easily manipulated by the principles disclosed herein. Namely, the fluoride example used herein is meant to explain the subject matter and is not intended as a limitation. In some embodiments, tooth enamel can form a fine network potential for diffusions in the inter- and intrarod prism. Metastable excess of water in enamel can contribute in a large part to the transport of particles through enamel. Most of the water content in the intercrystalline spaces of enamel can be presumed to exist as free water and only a small amount is present in form of hydroxyl groups. Furthermore, water desorption from micropores may not be easy, thus providing a network of fluidic channels through which AC electrokinetic drug transport could be mediated.

Referring back to FIG. 2B, tray 202 can be filled with fluoride gel and inserted orally into a patient's mouth PM. As such, fluoride particles can become suspended in tray 202 around the teeth's enamel. When an AC signal is applied to IDE arrays 204, re-distribution of the electrical charges in the fluoride particles suspended in the patient's bodily fluid (e.g. saliva) can establish net charges at the interface between the particle and the fluid, and forms an induced dipole across the particle. The induced dipole tends to align with the applied field.

The induced dipole moment, $\vec{p}$, and the dielectrophoretic force $\vec{F}$, are given by:

$$\vec{p} = 4\pi a^3 \varepsilon_m \left[ \frac{\varepsilon_p - \varepsilon_m}{\varepsilon_p + 2\varepsilon_m} \right] \vec{E} \tag{1}$$

$$\vec{F} = (\vec{p} \cdot \nabla)\vec{E} = 2\pi a^3 \varepsilon_m \left[ \frac{\varepsilon_p - \varepsilon_m}{\varepsilon_p + 2\varepsilon_m} \right] \nabla \vec{E}^2 \tag{2}$$

in which a is the radius of the particle, $\vec{E}$ is the applied electric field vector, and $\in_m$ and $\in_p$ are the dielectric permittivity of the fluid medium and the particle, respectively. If the applied field is non-uniform ($\nabla \vec{E} \neq 0$), the particle will experience a net force and move by the process of dielectrophoresis. Dielectrophoresis takes place in both DC and AC electric fields. Sustained particle motion only occurs in AC DEP with the appropriate driving frequencies, for which case, the permittivity in equation (2) is replaced by the frequency-related counterpart:

$$\tilde{\varepsilon} = \varepsilon - i\frac{\sigma}{\omega} \tag{3}$$

in which $\in$ and σ are the permittivity and electrical conductivity of the dielectric materials, and ω is the angular frequency of the electric field. While the particle travels via DEP in a surrounding fluid, the particle suffers a retarding drag force if the fluid is either moving slower than the particle or otherwise stationary. The fluid surrounding the particle is in turn dragged by viscous effects to accelerate in the same direction as the particle. The momentum exchange between the particle and the fluid reduces the velocity lag between the phases and eventually leads to an equilibrium state. A steady flow field can then be established around the particle in the fluid as a result of this hydrodynamic interaction. In a particle suspension, the particles further interact hydrodynamically with neighboring particles. Consequently, the induced flow field is intensified and an appreciable net flow is produced by the collective pumping action. This is the basic electromechanical transport process underlying the DEP-induced pumping technique in this device.

The AC dielectrophoretic force on the particle can be expressed using the frequency-dependent permittivity as:

$$\vec{F} = 2\pi a^3 \varepsilon_m \left( \frac{\tilde{\varepsilon}_p - \tilde{\varepsilon}_m}{\tilde{\varepsilon}_p + 2\tilde{\varepsilon}_m} \right) \vec{\nabla E}^2 \quad (4)$$

The complex relative permittivity is also referred to as the Clausius-Mossotti factor, $f_{CM}$, $$\tilde{f}_{CM} = \frac{\tilde{\varepsilon}_p - \tilde{\varepsilon}_m}{\tilde{\varepsilon}_p + 2\tilde{\varepsilon}_m} \quad (5)$$

Dielectrophoresis

In some embodiments, DEP can cause a translation of neutral particles towards or away from localized regions of high field intensity due to their polarization under a non-uniform electric field. DEP can enable a highly selective trapping of nanostructures based on the characteristic frequency response of the conductivity and dielectric permittivity of the particle versus those of the media. A dielectrophoretic force, $\vec{F}_{DEP}$, exerted by the field on a polarizable spherical particle in a surrounding medium, may be approximated by the equation:

$$\vec{F}_{DEP} = 2\pi r^3 \varepsilon_m Re[f_{CM}] \nabla E_{rms}^2$$

where, $\varepsilon_m$ is the permittivity of the suspending medium; $\nabla E_{rms}^2$ is the root mean square value of the gradient of the squared electric field; $Re[f_{CM}]$ is the real part of the "Clausius-Mossotti" factor given by the equation:

$$f_{CM} = Re\left[ \frac{\varepsilon_p^* - \varepsilon_m^*}{\varepsilon_p^* + 2\varepsilon_m^*} \right]$$

where $\varepsilon^*_p$ and $\varepsilon^*_m$ are the complex permitivities of the particle and the suspending medium, respectively, defined as $\varepsilon^* = \varepsilon - (j\sigma/\omega)$ where $\sigma$ is the electrical conductivity and $\omega$ is the angular frequency of the applied electric field, respectively, and $j=\sqrt{-1}$.

The dielectrophoretic force can dependent on the intensity of the electric field (E), but also on the radius of the particle (r). The frequency dependence of $Re[f_{CM}]$ indicates the force acting on the particle can vary with the frequency. At frequencies below 50 KHz and, specifically, for the frequency range used in this application, the DEP force can depend chiefly on the conductive properties of the particle ($\sigma_p$) and suspending medium ($\sigma_m$) where, $$Re[f_{CM}] \approx [(\sigma_p - \sigma_m)/(\sigma_p + 2\sigma_m)]$$

Fluoride gels can comprise chiefly DI water (95%) and the fluoride particles (2.7%) can be highly conductive, due to their ionic solid crystal structure. For highly conductive particles in an insulating media, the double-layer screens at low frequency can cause a negative DEP (nDEP), with particle polarization occurring at Kilo Hertz level to cause a positive DEP (pDEP). Because the complex permittivity $\varepsilon^* = \varepsilon + (\sigma/j\omega)$ for most particles, at low frequencies (up to 1 MHz), electrical conductivity $(\sigma/j\omega) >> \varepsilon$, and therefore can dominate the complex permittivity $\varepsilon^*$ or the DEP behavior. As such, DEP forces affecting the movement of fluoride particles in a nonuniform electric field can be exploited to enhance fluoride transport into enamel at various frequencies. Fluoride particles can be separated from gel excipients by the positive DEP forces and dragged to the enamel surface by additional AC electromotive forces to concentrate the particles at the enamel pores.

Assuming the electric field varies with a single angular frequency w, the time-averaged dielectrophoretic force can be computed as:

$$\langle \vec{F}_{DEP} \rangle = \pi a^3 \varepsilon_m Re[f_{CM}] \nabla |\vec{E}|^2 + 2\pi a^3 \varepsilon_m Im[f_{CM}](E_x^2 \nabla \phi_x + E_y^2 \nabla \phi_y + E_z^2 \nabla \phi_z) \quad (6)$$

where $Re[f_{CM}]$ and $Im[f_{CM}]$ denote the real and imaginary parts of $f_{CM}$, and $E_x$, $E_y$ and $E_z$ are components of the electric field vector; $\phi_x$, $\phi_y$, and $\phi_z$ are the phase angles if the electric field is spatially phase-shifted. The DEP force depends on the spatial non-uniformities in both the field strength $(\nabla(|\vec{E}|^2))$ and the phase $\nabla\phi$. The first term on the RHS of equation (6) determines the alignment of the DEP force with respect to the maxima/minima of the electric field and is the regular DEP force component in DC DEP. The second term on the RHS of equation (6) only appears if the electric field has a spatially varying phase, such as in a traveling-wave field, and therefore is the traveling-wave DEP (twDEP) force component.

In some embodiments, particles can experience a DEP force in a non-uniform electric field and the DEP force does not depend on the field polarity. If the electric field is uniform, then the force acting on each of the poles of the induced dipole within the particles is equal and opposite and there is no net motion of the particle. Particle movement in field gradients can occur because the forces acting on the two poles are not identical due to the gradient in the field. Particles that are more polarizable than the media ($Re[f_{CM}] > 0$) can be pulled along the gradient into areas of highest field intensities (positive DEP). Particles that are less polarizable than the media ($Re[f_{CM}] < 0$) are pushed away from these areas (negative DEP). As such, dielectrophoresis can allow for collection of particles or their levitation above the electrodes.)

The alignment of the DEP force with the applied field is contingent upon the Clausius-Mossotti factor $f_{CM}$, which is frequency-dependent. In this application, the real and imaginary parts of $f_{CM}$ are a function of the frequency of the applied field for fluoride particles suspended in water. $Re[f_{CM}]$ is negative in the low-frequency range (f<100 Hz) in which the particles are less polarizable than the surrounding fluid, and crosses over to positive values as the frequency increases (f>100 Hz) and the particles become more polarizable than the fluid. If $Re[f_{CM}] > 0$, the regular DEP force component aligns favorably with the field strength gradient. As a result, the particles move towards the maxima of the electric field, which are usually located at the edges of the electrodes that are used to generate the electric field, and positive DEP occurs. In the opposite situation, a negative $Re[f_{CM}]$ brings about negative DEP (nDEP) where the particles move away from the maxima of the electric field, distancing themselves from the electrodes. $Im[f_{CM}]$ vanishes at both extremes of the frequency spectrum. The nDEP force is generally oriented perpendicular to the electrode plane, resulting in levitation and translation away from the electrode surface. As such, the criteria for effective nDEP are $Re[f_{CM}] < 0$, which correlates to a specific spectrum or range of frequencies unique to the fluoride gel that fulfill the criteria.

The electric field needed for nDEP can be generated by applying a sinusoidal-wave voltage signal to specially designed electrode arrays. In other embodiments, the signal can be sinusoidal, square, triangular, or pulse in nature. Three planar parallel electrodes as shown in FIG. 1D can be integrated into a thermoplastic intraoral fluoride tray that fit over and conform substantially to the shape of the teeth (see, for example, FIGS. 2A-2C). In some embodiments, the electrodes can be 3 cm long and have width and uniform spacing of $d_1$ (width)=30 mm and $d_2$ (i.e., the distance between the tip of a finger and outer edge of an IDE array)=(30) µm, respectively. If the fluid (gel) and particles (fluoride) are assumed to be homogeneous linear dielectric materials, the electric field in the particle suspension in the gel tray can be solved using Laplace's equation.

A commercial software package, FLUENT (available from ANSYS, Inc., Canonsburg, Pa., United States of America), can be used to simulate the electrical field by solving scalar transport equations. The electric potential for an AC field of angular frequency ω is:

$$\phi(\vec{x},t)=\phi_1 \cos(\omega t)+\phi_2 \sin(\omega t)$$

where both $\phi_1(x,y)$ and $\phi_2(x,y)$ satisfy Laplace's equation $\nabla^2 \phi_i=0$ (i=1, 2). After solving for the electric potential, the electric field is obtained from $\vec{E}(\vec{x},t)=-\nabla\phi=\vec{E}_1(x,y)\cos(\omega t)+\vec{E}_2(x,y)\sin(\omega t)$, where $\vec{E}_1(x,y)=-\nabla\phi_1$ and $\vec{E}_2(x,y)=-\nabla\phi_2$.

Once the traveling-wave electric field is solved, the time-averaged DEP force can be recast in the following form:

$$\langle \vec{F}_{DEP} \rangle = \pi a^3 \in_x Re[f_{CM}] \vec{\nabla}(E_{x1}^2+E_{x2}^2+E_{y1}^2+E_{y2}^2)+2\pi a^3 \in_x Im[f_{CM}](E_{x1}\vec{\nabla}E_{x2}-E_{x2}\vec{\nabla}E_{x1}+E_{y1}\vec{\nabla}E_{y2}-E_{y2}\vec{\nabla}E_{y1})$$

in which $E_{x1}$ and $E_{y1}$ correspond to $\phi_1$, and $E_{x2}$ and $E_{y2}$ correspond to $\phi_2$. The first term which is the regular DEP force component controls the vertical motion of the particle, while the second term which is the traveling-wave DEP (twDEP) force component is responsible for additional particle motion in the tangential direction. These two force components together can give rise to the DEP-based microfluidic pumping. Negative DEP Force is required for twDEP to occur. As a result, a particle suspended in the fluid can levitate away from the electrode surface making the vertical motion of the particle possible. To render the problem tractable, rotational motion and Brownian dynamics can be neglected. The coupling of nDEP and twDEP with AC electroosmosis is not considered in transport outside of the tooth, since they are effective at different frequency ranges and AC electroosmosis is exploited inside the tooth. The geometry of the electrode array, including the electrode width and spacing, can be optimized together with the particle concentration to produce higher flow velocity.

These DEP concepts can be extended to 3-D, where electric fields can varyingly extend into the vertical axis. When considering vertical forces, the buoyancy force (FB) of the particles can be accounted for as well:

$$F_B=4/3\pi r^S(\rho_p-\rho_m)g$$

where r is the radius of the particle and $\rho_p$ and $\rho_m$ are the densities of the particle and medium, respectively. The buoyancy force can act with or against the vertical DEP force, depending on the orientation. At a certain point between two electrodes, the vertical DEP force and buoyancy force will be in equilibrium, allowing particles to suspend in the solution above the surface. The particles oscillate a little around their equilibrium positions due to Brownian motion.

Once a high-frequency signal is applied, the particles collect at the edge of the electrode, designating the occurrence of positive DEP. Upon decreasing the frequency, a negative DEP force can cause the particles to be repelled from the electrode to the gap region. If the frequency falls in the effective twDEP range, the particles experience traveling-wave DEP forces and travel in the transverse plane parallel to the microelectrode array. In this system, the traveling-wave DEP component is an additional driving force for particle motion. Therefore, the velocity lag can be estimated from:

$$|\vec{u}_p - \vec{u}_m| \cong \left|\frac{\vec{F}_{mDEP}}{6\pi\mu_f a}\right|$$

where:

$$\vec{F}_{mDEP} = 2\pi a^3 \varepsilon_m \text{Im}[f_{CM}](E_x^2 \nabla \varphi_x + E_y^2 \nabla \varphi_y + E_z^2 \nabla \varphi_z)$$

The DEP induced flow field can be analyzed with a numerical model to study the flow physics for particle suspensions. The electric and the flow fields can be decoupled from each other and solved sequentially using the commercial software package, FLUENT. The solution of the electric field can yield the DEP forces. This DEP force can then introduced as a body force in the Navier-Stokes equations to solve for the induced flow field. By following this procedure, the complex solid-liquid two-phase flow problem can be converted to a single-phase fluid flow problem. The simulations can predict the effects of varying the frequency and voltage of the applied field on the induced flow field. For the selected frequencies, the particles can experience both negative and traveling-wave DEP forces and for a given frequency, the velocity can increase both by increasing applied voltage and, by modulating the frequency of the electric field, even at lower voltages.

The electric field can be modeled by approximating the potential (V) applied based on equation below (den Otter):

$$V(x, y) = \frac{4V_o}{\pi} \sum_{n=1}^{\infty} \frac{1}{2n-1} * \sin\frac{(2n-1)\pi x}{a} * \exp\left(-(2n-1)*\pi*\frac{\text{abs}(y)}{a}\right) * BesselJ\left(\frac{(2n-1)\pi s}{2a}\right)$$

In one embodiment, this equation may be calculated using MAPLE 12 Software (Maplesoft, Waterloo, Ontario, Canada) where $V_o$=applied potential, x=the distance between two electrode fingers, a=the periodicity of the finger spacing, y=the height above the plane of the electrode, s=spacing between two electrodes (100 µm), and n=the array size. As y increases, moving away from the electrode plane, the voltage decays in a nonlinear manner so that ~150 µm above the electrode, the electric field is negligible.

Once the dipole moment of the active agent (e.g., fluoride particle), the target distance, drag velocity of the suspending medium etc., have been calculated, the aforementioned formulas can predict the strength of the electric field required to get the active agent (e.g., fluoride particle) to move. The conductivity and other dielectric information (e.g., permittivity) of the fluoride gel can also be collected to determine the optimal operation frequencies which will motivate the fluoride into the tooth.

In some embodiments, dielectric measurements can be carried out using a dielectric analyzer (DEA) 2970 from TA Instruments, New Castle, Del., United States of America, using a ceramic single surface cell of 20×25 mm$^2$ based on a coplanar interdigitated comb-like electrode design. The sensors can be calibrated for every experiment. All the experiments can be performed under a dry nitrogen atmosphere at a gas flow rate of 50 mL/min. The experiments can be carried out at 12 different frequencies in the range from 0.01 Hz to 100 KHz. The total time taken to scan all the different frequencies is 1.2 min.

The principle of this technique can include placing a sample under an alternative voltage and measuring the resulting current and the phase angle shift induced. The measured current can be separated into its capacitive and conductive components. An equivalent capacitance and conductance can then be calculated and used to determine the dielectric permittivity $\in'$ and the dielectric loss factor $\in''$. Dielectric permittivity $\in'$ is proportional to capacitance and measures the alignment of dipoles. Factor $\in''$ is proportional to conductance and represents the energy required to align dipoles and move ions. Ionic conductivity is calculated as follows: $\sigma = \in_0 \in'' \omega$ (2) where $\in_0$ is the absolute permittivity of the free space ($8.85 \times 10^{-12}$ F/m) and $\omega$ ($2\pi f$) is the pulsation of the applied potential difference. When $\in''$ is controlled by conductivity, equation (2) can be used to calculate $\sigma$.

In some embodiments, a dielectric analyzer (e.g., a TA Instrument Dielectric Analyzer 2970) can be used to measure the capacitive and conductive properties of the drug over a wide range of frequencies. The capacitive nature of a material is its ability to store electrical charge, and the conductive nature is its ability to transfer an electric charge. These electrical properties can be related to molecular activity, allowing for molecular mobility of drugs and polymers.

In a representative experiment, a 5 mg sample of the drug was deposited on a single surface gold ceramic diffusion cell for analysis. The entire arrangement was placed in a DEA furnace chamber and brought to 37° C. An AC source was cycled through a range of frequencies from 0.1 Hz to 100,000 Hz. The induced current and phasing in the sample and permittivity information at each frequency was monitored and collected. The characteristic frequencies were identified by plotting the log of conductivity against the log of frequency.

In some embodiments, the ideal low and high transport frequencies to load the fluoride into enamel can be determined, however, by an algorithm plotting out conductivity of fluoride gel against a wide range of frequencies 0.1 to 100,000 Hz after conducting four point analysis (or impedance spectroscopy).

Four Point Conductivity Analysis

In some embodiments, the capacitive and conductive properties of the sodium fluoride particle-containing gel can be measured over a frequency range from 0.1 Hz to 100 KHz, using a four point probe connected to an Agilent 4156C analyzer (Agilent Technologies Inc., Santa Clara, Calif., United States of America). The composition of the gel can be 2.7% NaF and 95% water as per manufacturer's spec list. Water can be used to estimate the conductive properties of the medium, and the actual dielectric properties of the gel to estimate sodium fluoride particle conductivity. Four equally spaced probes can be dipped in the fluoride gel to carry out impedance spectroscopy. Two probes can be used for sourcing current and two probes for measuring voltage drop. The induced current and phasing in the sample and permittivity information at each frequency can be collected. The conductivity can be plotted as a function of frequency and an optimal motivating frequency between 100 Hz and 100,000 Hz was then selected, where conductivity is relatively high and constant, or the impedance is low and constant. An optimal orienting frequency can be selected between 0.1 Hz and 100 Hz, where capacitance is relatively high and constant. The particle conductivity ($\sigma_p$, $1/\Omega \cdot cm$ or S/cm) at each frequency can be determined by the equation $\sigma = L/(width \cdot R \cdot depth)$, where the length (L), width and depth are parameters of the fluoride gel containing vessel and R is the resistance value at each frequency. The capacitance of the fluoride particles in the gel at each frequency was determined by the equation: $X_C = 1/\omega C$, where $X_C$ is the impedance (in ohms), $\omega$ is the angular frequency ($2\pi f$) and C is capacitance in farads.

In some embodiments, the impedance measurements can be assumed to be related to fluoride particles since the composition of the gel is primarily DI water and fluoride particles. Furthermore, impedance spectroscopy data can be analyzed employing electrical circuit models. The current system can be composed of conductive sodium fluoride particles within a highly insulating media (DI water with media conductivity of 0.1 mS/m). The equivalent circuit can be composed of a pathway due to solution resistance in parallel to another pathway dominated by electrical parameters of the particle. Since solution resistance is much higher than that of the particles (as explained above), the current through this shunt resistance to the solution can be kept minimal and a majority of the current can be directed through the particle pathway. As such, particle properties such as double-layer screening and particle polarization will dominate the four point conductivity analysis.

Figure 3A:
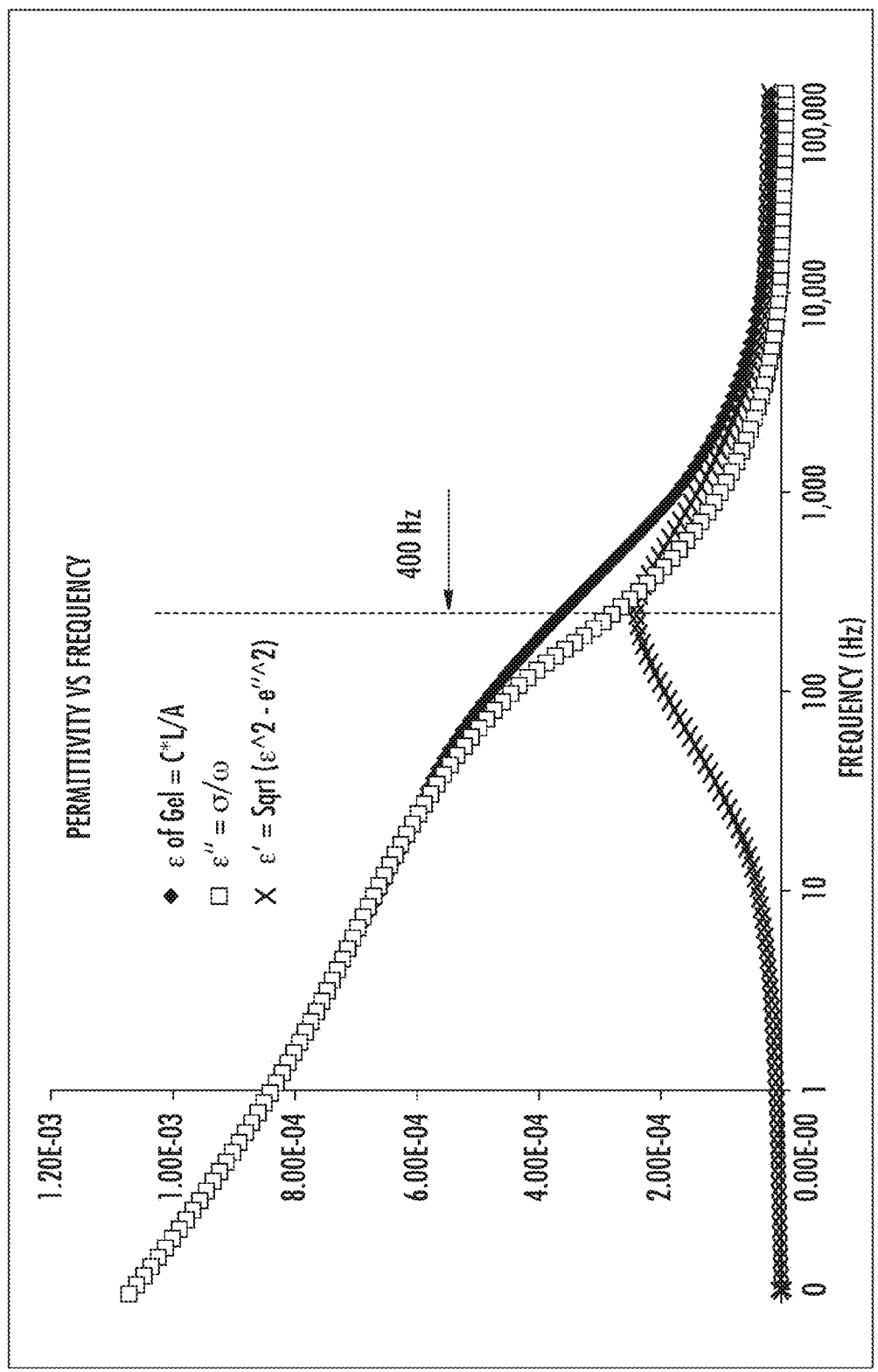
FIG. 3A to 3C are exemplary frequency plots of the frequency signals being applied to the interdigitated array electrode electrodes in accordance with aspects of the subject matter described herein.
Figure 3B:
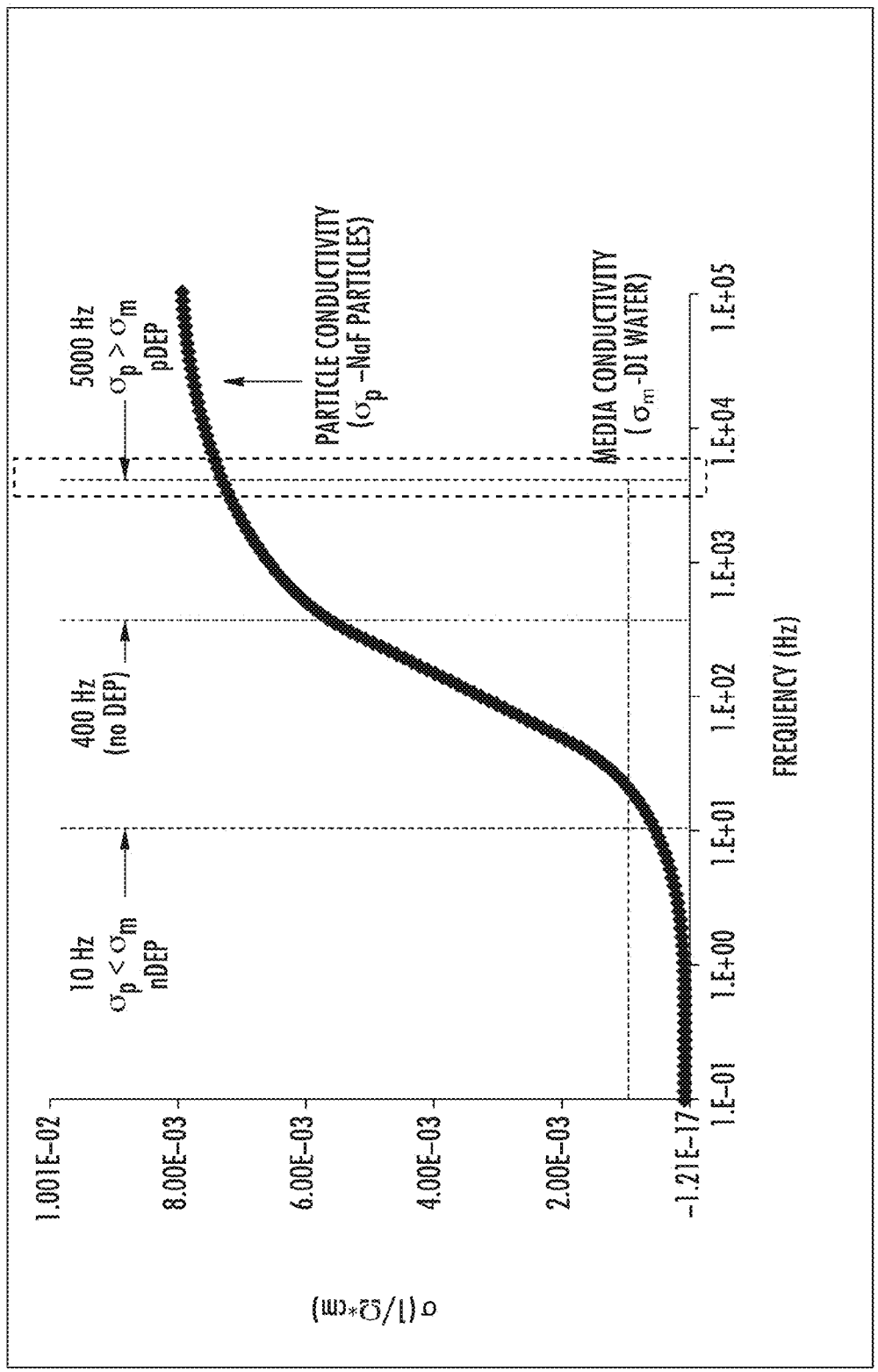
Figure 3C:
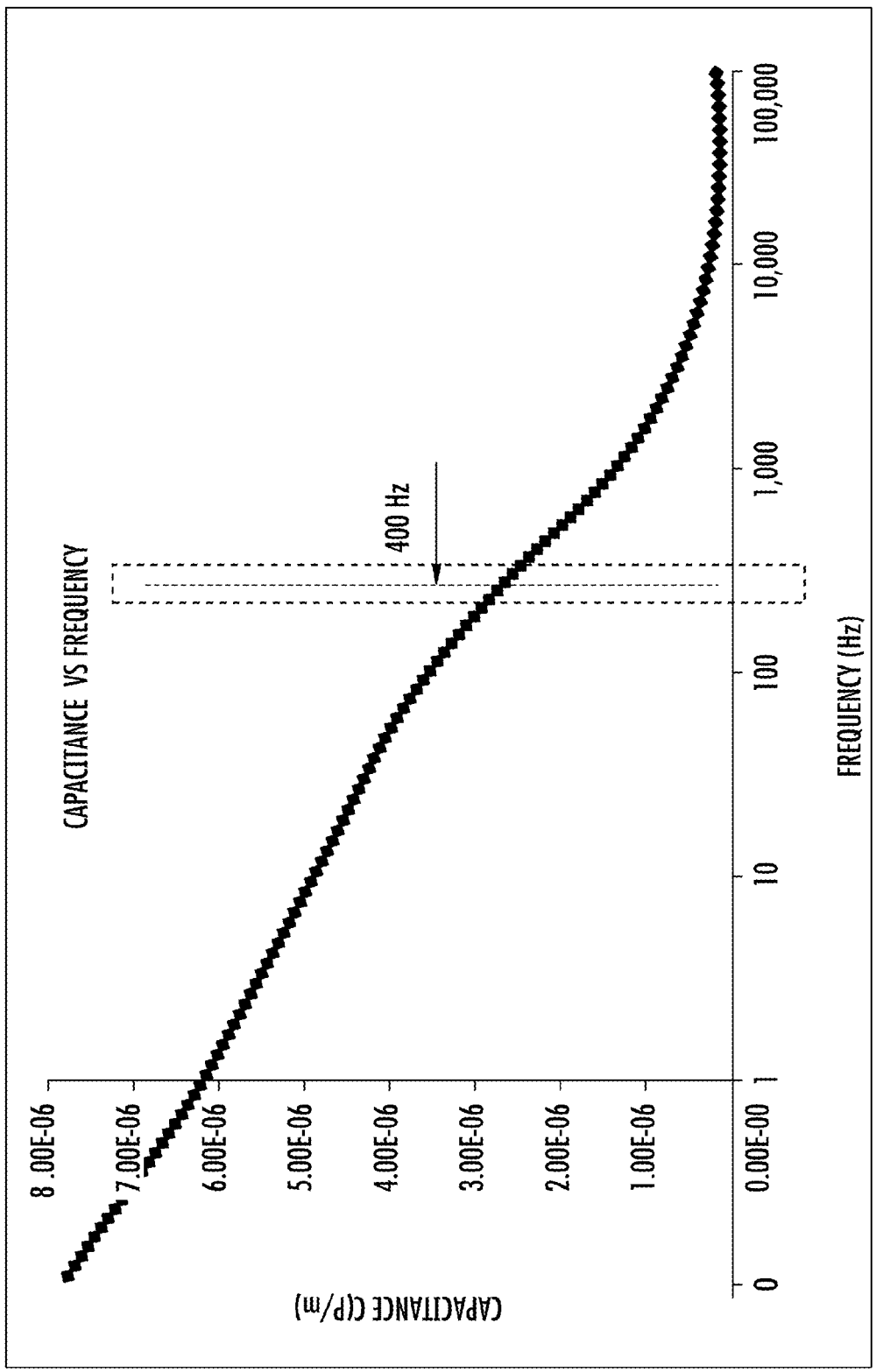

Furthermore, utilizing this technique, optimal frequencies for this particular application can be determined to be 10 Hz and 5000 Hz, and the current generated can be 0.01-0.03 mAmp. Furthermore, as shown in FIG. 3B and FIG. 3C, given that particle mobility µ is directly proportional to absolute permittivity $\in$, the spike in absolute permittivity at 400 Hz in FIG. 3A, which also coincides with an inflection in the conductivity and capacitance curves, suggested that ACEO particle mobility can be favorable at 400 HZ and likely an optimal ACEO frequency. (See discussion on ACEO)

In some embodiments, to identify the appropriate frequencies for nDEP and pDEP behavior, the frequency response of the conductivity of sodium fluoride particles can be measured as a function of frequency. As indicated by the graph in FIG. 3B, the particle conductivity rises steadily from 10 Hz onwards and begins to plateau beyond 5 kHz. Taking a media conductivity ($\sigma_m$) for the aqueous media at about $10^{-4}$ S/cm, nDEP behavior ($\sigma_p < \sigma_m$) is expected at frequencies of 10 Hz or below and strong pDEP behavior ($\sigma_p > \sigma_m$) at frequencies of 5 kHz or above. Upon applying fields of 5 $V_{pp}$/mm at 10 Hz, the particles can be translated away from the electrode edges and the particles can be collected within a characteristic region away from the electrode indicating nDEP behavior. Upon applying fields of 5 $V_{pp}$/mm at 5000 Hz, the particles can be translated towards the electrode edges and the particles are collected within a characteristic region at the electrode edge indicating pDEP behavior.

In some embodiments, it can be confirmed that the fluoride particles can be translated towards and away from respective electrode edges under frequency-modulated DEP forces. Alternatively, because DEP forces are highly localized, there can be a need for an alternate set of longer-range translation forces that are capable of driving the fluoride particles from the proximal IDE array into the adjoining porous enamel layer to depths of 10-300 µm. Since ACEO can generate vortices within the fluid that act to drag pDEP trapped particles away from the electrode edges, it is likely to generate more long range particle translation and thereby cause enhanced penetration of particles into the porous enamel. For example, fields of 5 $V_{pp}$/mm at 400 Hz can cause translation of particles vertically away from the edges of the distal electrode. In some embodiments, particles can be driven 10-100 µm away from the electrode plane.

In some embodiments, the sodium fluoride gel sample, which is suspended in aqueous media, can be a highly conductive ionic solid material composed of about 10 µm sized particles. At low frequencies, the double-layer around the particles screens the applied field thereby can cause a nDEP behavior. At frequencies faster than the double-layer relaxation time, the double-layer may no longer be able to screen the external field, which can result in a pDEP behavior. While negative DEP is usually caused by permittivity effects, where media permittivity dominates over that of the particle, double-layer polarization in the lower frequency range can cause negative DEP due to screening of particle polarization. As such, a crossover can result from negative DEP at low frequencies to positive DEP at higher frequencies.

Optical Microscopy of Fluoride Particles

In some embodiments, images of real-time translation of the fluoride particles under the electric field at particular frequencies, stacked optical images can be acquired using a Zeiss PrimoVert Light Microscope with an AxioCam ERc5s camera and Zen 2011 software (Carl Zeiss Microscopy, LLC, Thornwood, N.Y., USA). The real time images can be taken at 10×-MPF with a 1799.95 μm range at numerical lens aperture 0.55 mm and working distance (WD) 26 mm. Each image can be reconstructed from 450 slices taken at 4 μm intervals. Uniform thickness of the gel sample between electrode plates and cover slip glass can be verified. The respective focus positions of the electrode and the fluoride particles in the media can be used to evaluate vertical displacements of the particles under DEP and ACEO.

Experimental Design for Fluoride Deposition on Enamel

In some embodiments, tests can be conducted to image the dielectrophoretic translation of sodium fluoride particles using single frequencies on the terminals of the IDE array. After optimizing the frequencies for particle translation under nDEP, pDEP and ACEO, the following procedure was used to deposit fluoride by DEP coupled to ACEO.

Deposition of Fluoride Particles into Enamel

In some embodiments, after confirming nDEP behavior of the fluoride particles at 10 Hz, pDEP behavior at 5000 Hz, and vertical translation above the electrode plane by ACEO at 400 Hz, these frequencies can be applied successively within an assembly. The 10 Hz frequency was applied between the reference electrode and the distal IDE to initiate nDEP, followed by 5000 Hz between the distal and proximal IDEs to initiate pDEP, followed by 400 Hz between the electrodes of the proximal IDE to initiate ACEO. Images of particle deposition into the enamel pores can be taken with an electron microscope to visualize, and wavelength dispersive spectrometry (WDS) can be used to measure the penetration of fluoride particles within the enamel rod pores. While the fluoride particles translated towards the enamel are larger (ca. 10 μm), the crystals break down as they diffuse into the enamel rod and react with hydroxyapatite to give fluorapatite according to the chemical reaction: $2NaF+Ca_{10}(PO_4)_6(OH)_2 \rightarrow Ca_{10}(PO_4)_6F_2+2NaOH$. As a result, the particle sizes on enamel are smaller than the particles within the gel.

Enhancing Penetration of Fluoride into Enamel

In some embodiments, following the optimization of deposition conditions, the fluoride particles may be driven to deposit onto the enamel. This involved translating the fluoride particles under nDEP conditions of 5 $V_{pp}$/mm at 10 Hz, applied first between a Cu plate electrode and the distal IDE array to drive the particles away from the Cu plate and then, as a co-planar field, between the electrodes of the proximal IDE to drive the particles away from the electrode edges. This can be followed by a cross-planar field of 5 $V_{pp}$/mm at 5000 Hz between the distal and proximal IDE array to drive the particles through the open slots and a co-planar field of 5 $V_{pp}$/mm at 400 Hz between the electrodes of the proximal IDE array) to cause the translation of particles vertically away from the edges of the distal electrode edges and into the adjoining pores of the enamel surface. The fields were applied successively using these four circuits.

In some embodiments, based on measurements of particle conductivity and imaging of the translation of approximately 10 μm sized sodium fluoride particles in the aqueous gel media under electric fields at various frequencies, the study confirmed that 5 $V_{pp}$/mm fields caused nDEP behavior at 10 Hz frequency and pDEP behavior at 5000 Hz frequency. The particle translation over distances of about tens of microns above the plane of the electrode under a field of 5 $V_{pp}$/mm at 400 Hz, as confirmed by z-stacks, can be attributed to ACEO. This may be caused by a critical frequency at which ACEO dominates. As such, while velocity due to ACEO can increase as the frequency is lowered from the point of discernible pDEP, this velocity can reach a maximum and then reduces with a further decrease in frequency. In some embodiments, the maximum ACEO vortices can be at approximately 400 Hz. Real-time microscopy can be utilized to confirm particle motion under the various AC fields applied herein. At 10 Hz frequency, particles lining up away from the electrode and above the electrode plane are consistent with nDEP at this frequency. At higher frequencies, pDEP at 5000 Hz and ACEO at 400 Hz was observed.

In some embodiments, based on the fluoride uptake data, DEP-induced deposition at 10 Hz can initiate a nDEP behavior and 5000 Hz can initiate a pDEP behavior, causing a doubling of fluoride content in the initial 10-20 μm layer of the enamel. Upon the application of DEP in combination with the field at 400 Hz to initiate ACEO, the fluoride penetration can be apparent up to depths of 300 μm. While the DEP action is highly localized at the electrode edges, the longer range action of the vortices set-up under ACEO can drag the fluoride particles trapped by DEP at the electrode edges towards the electrode center and upwards, thereby causing a higher degree of fluoride penetration into the enamel. The observation presented herein on the longer range action of DEP when applied in combination with ACEO is consistent with prior work, and the novelty of the current work lies chiefly in its application towards enhancing the penetration of fluoride particles into enamel.

As such, as shown in FIG. 3B, an optimal orienting/motivating frequency was selected from the plot as a high operating frequency value between 100 Hz and 100,000 Hz, where conductivity is relatively high and constant, or the impedance is low and constant. Similarly, an optimal low (orienting/motivating) operating frequency was selected as a frequency value between 0.1 Hz and 100 Hz, where capacitance is relatively high and constant (FIG. 3C). The signal was then applied to the IDE array assembly by the signal generator which is programmed to continually cycle the two frequencies. In this experiment, optimal high (5000 Hz) and low (10 Hz) frequencies were chosen from Debye plots. Further, as shown in (permittivity vs frequency curves) FIG. 3A given that particle mobility μ is directly proportional to absolute permittivity ∈, the spike in absolute permittivity at 400 Hz, which also coincides with an inflection in the conductivity (FIG. 3B) and capacitance (FIG. 3C) curves, suggested that ACEO particle mobility would be favorable at 400 HZ.

Referring back to FIG. 1D, a DEP fluoride pumping prototype can include two arrays of IDEs that are fabricated using photolithography in some embodiments of the disclose subject matter. The IDE electrodes can be made out of a layer of (30) μm thick gold on a flexible PCB board. Each array can contain (e.g., 14 pairs) parallel thin-bar (finger) microelectrodes that are each 250 μm wide. The fingers (e.g., 14 pairs per electrode) can be separated by intervals of 1 mm containing interstitial spaces 0.5 mm wide. The rather large gap may be selected in order to reduce electrical leakage between electrodes, to alleviate electrothermal effects caused by Joule heating, and to allow a passage for drug flow. A layer of insulator (e.g., parylene C or polyimide with a thickness of 250 μm) can be deposited over the electrode array to avoid electrolysis and corrosion of the electrodes when the device is in contact with the particle suspensions.

The DEP device can be mounted on a printed circuit board comprising polydimethylsiloxane (PDMS) or SU8 by single step photolithography and the electrodes connected to an AC voltage of frequency f. In the stationary set up, the applied electric signals can be controlled by a pulse generator (e.g., Wavetech or Berkeley Nucleonics Model 565, Berkeley Nucleonics, San Rafael, Calif., United States of America) and/or a custom-built timing circuit or a multi-channel function generator (e.g., a TGA1244 signal generator, Thurlby Thandar Instruments Limited, Cambridgeshire, United Kingdom) The applied voltage can range from 0 to 10 V, with frequencies ranging from 0.1 Hz to 100 kHz. A digital oscilloscope (e.g., Tektronix TDS 3032B, Beaverton, Oreg., United States of America) can used to monitor the frequency and waveform of the applied signals during the experiments.

Figure 4A:
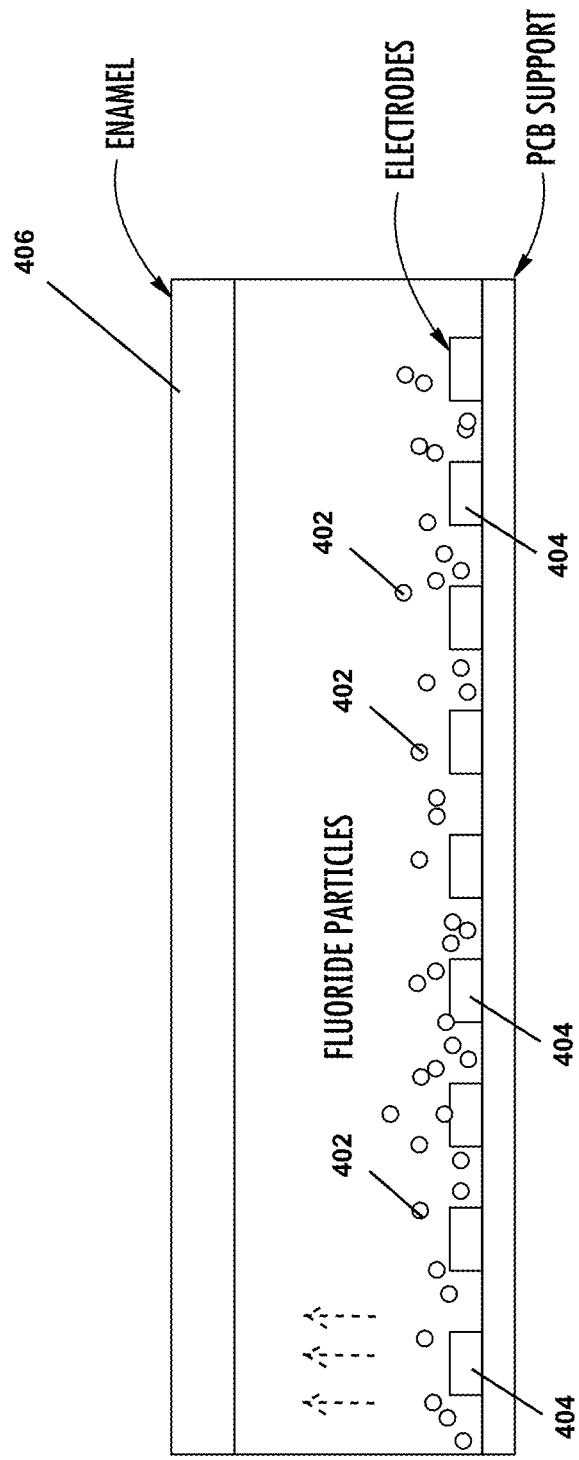
FIG. 4A is an exemplary illustration of fluoride particles coming in contact with tooth enamel in accordance with the subject matte disclosed herein.

Once a critical high-frequency signal (e.g., 5000 Hz) is applied, the fluoride particles can collect at the edge of the electrode, thereby designating the occurrence of positive DEP. Upon decreasing the frequency to 10 Hz, a negative DEP force can cause the fluoride particles to be repelled from the electrode to the gap region. As shown in FIG. 4A, when the frequency falls in the effective nDEP range, particles 402 (e.g., fluoride particles) can experience the nDEP forces and travel in both the perpendicular plane and the transverse plane perpendicular to an IDE array 404 and towards enamel 406. It should be noted that the nDEP component is the primary driving force for particle motion in FIG. 4A.

ACEO

In some electrode configurations, AC fields can also induce fluid flows by ACEO. ACEO can generate fluid motion by inducing mobile charges in the double layers. When a small AC signal is applied over an electrode pair, the electrode surfaces can become capacitively charged by forming counter-ion accumulation. The counter-ions can migrate with or against an electric field ($E_t$) that is tangential to the electrode surface, which can in turn produces a fluid motion due to fluid viscosity (η). The fluid velocity in AC electroosmosis <u> is potential (ψ) and frequency (ω) dependent and can be expressed by, $$\langle u \rangle = \frac{1}{2}\text{Re}\left[\frac{\varepsilon E_\tau(\psi)\omega}{\eta}\right]$$

ACEO can occur between the frequencies of 10 Hz and 10 kHz (e.g., less than 10 kHz). ACEO can flow in a recirculating fashion, but asymmetric electrode patterns can be configured to produce flows that can be used for microfluidic pumping, as well as to generate local and bulk liquid flow. At applied potentials from 0.1 to 10 V, planar asymmetric electrodes can produce flows that are capable of transporting particles.

In some embodiments, electroosmosis can be the process of using DC potential to moving fluids through a porous medium. As with EO, ACEO is also based on the ion migration within a nanometer layer of charges/ions at the interfaces of electrolytes and solids (double layer). This layer of charges can migrate under electric fields tangential to the interface, and because of fluid viscosity, the ion movement carries along its surrounding fluids, leading to fluid motion. In ACEO, the charges in the double layer can be induced by AC potentials, and tangential E-fields can also form from the same voltage source. Therefore, the changes of polarities in charges and field directions are simultaneous and cancelled out, maintaining steady ion migration and fluid motion. By adjusting the amplitude and frequency of AC signals, a variety of directed surface flows can be produced on electrodes to manipulate and transport particles. In symmetric systems (both spatial and temporal) the resulting liquid flow can alternate in direction with a zero offset. To obtain directionality asymmetry can be added either in space (by electrode geometry) or in time (by applying asymmetric AC signals).

When a liquid comes into contact with a solid, the formation of an interfacial charge can cause a rearrangement of the local free ions in the liquid so as to produce a thin region of non-zero net charge density, commonly referred to as the electrical double layer (EDL), near the interface. The application of an external electric field can result in a net body force on the free ions within the EDL inducing a bulk fluid motion called electroosmotic flow. For pure electroosmotic flows (i.e., absent of any pressure gradients) of incompressible liquids, the Navier-Stokes equations can take the following form:

$$\rho_f t \frac{\partial v}{\partial t} = \mu \nabla^2 v + \rho_e E(\omega t)$$

where v is the flow velocity, t is time, $\rho_f$ is the fluid density, $\rho_e$ is the net charge density, μ is the fluid viscosity, and E(ωt) is a general time periodic function with a frequency ω=2πf which describes the applied electric field strength.

For a rectangular microchannel model, the electric double-layer distribution, ψ, can in its most general form be described by the Poisson equation:

$$\in \nabla^2 \psi = \rho_e$$

where $\in$ is the dielectric constant of the fluid medium. In the absence of a significant convective or electrophoretic disturbance to the double layer, the net charge density field can be described by a Boltzmann distribution, which takes the form (assuming a symmetric electrolyte):

$$\rho_e = -2zen_0 \sinh\left(\frac{ze\psi}{k_b T}\right)$$

where z is the valence, e is the charge of an electron, $n_0$ is the bulk electrolyte concentration, $k_b$ is the Boltzmann constant, and T is the temperature. Combining the two formulas and introducing the non-dimensional double-layer potential, ψ=zeψ/$k_b$T, and nondimensional double-layer thickness K=Dh$_\kappa$ (where Dh is the hydraulic diameter of the channel, $D_h$=4$I_x I_y$/2($I_x$+$I_y$), and κ is the Debye-Hückel parameter) yields the nonlinear Poisson-Boltzmann distribution equation:

$$\nabla^2 \psi - K^2 \sin h(\psi) = 0$$

where the ~ signifies that the spatial variables in the gradient operator have been nondimensionalized with respect to Dh (i.e., X=x/$D_h$, Y=y/$D_h$). This equation can be subjected to the symmetry conditions along the channel center axes, ∂ψ/∂X=0 at X=0 and ∂ψ/∂Y=0 at Y=0, and the appropriate Dirichlet conditions at the channel walls, ψ=$Z_1$ at X=$L_x$/2 and ψ=$Z_2$ at Y=$L_y$/2 (where $Z_{1,2}$=ze$\zeta_{1,2}$/$k_b$T, $L_x$) $I_x$/$D_h$, and $L_y$) $I_y$/$D_h$).

In some embodiments, the capacitative and conductive properties of the fluid (e.g. fluoride gel) can be measured over a frequency range from 0.1 Hz to 100 KHz, using a four point probe that is connected to an analyzer device (e.g., Agilent 4156C analyzer, Agilent, Santa Clara, Calif., United States of America), referred to as a four point conductivity analysis. Four equally spaced probes can be dipped in the fluoride gel to carry out impedance spectroscopy. Two probes can be used for sourcing current and two probes for measuring voltage drop. The induced current and phasing in the sample at each frequency can be collected. Conductivity ($\sigma$; 1/P·cm or S/cm) at each frequency can be determined by the equation $\sigma=L/(width·R·depth)$, where the length (L), width and depth are parameters of the fluoride gel containing vessel and R is the resistance value at each frequency. The capacitance of the fluoride gel at each frequency can be determined by the equation: $XC=1/\omega C$, where XC is the impedance (in ohms), $\omega$ is the angular frequency ($2\pi f$) and C is capacitance in farads.

In some embodiments, an operating frequency to induce ACEO can be selected based on coincidental inflections in the conductivity, permittivity, and capacitance occurring at about 400 Hz, as shown in FIGS. 3B and 3C. Given that electroosmotic mobility can be directly proportional to permittivity and, in general, expressed by:

$$\mu \propto (\in \zeta/\eta) \cdot E_t$$

where $\mu$ is mobility, $\in$ is the permittivity of the medium, $E_t$ is the tangential electric field; and where $\zeta$ the Zeta potential and $\eta$ the viscosity of the gel are assumed to remain constant, the inflection in permittivity at 400 Hz suggests that fluid mobility would be favorable at 400 Hz.

In some embodiments, an intraoral delivery system can include two IDE arrays as described in FIG. 1D. An AC signal generated by a signal generator such as the DSP generator described in FIG. 1A can include an optimal low and high frequency, which can be delivered to the first two IDE's to generate a nDEP force to induce polarization and mobility of a substance outside the substrate (tooth); and a third signal at a third frequency delivered to the third IDE, specific to the targeted depth of the enamel substrate to enhance its permeability to the fluoride. For example, a 400 Hz ACEO signal can be electrically coupled to the second IDE to promote fluoride penetration to the tooth enamel at a depth of approximately 300 μm.

In some embodiments, the intraoral delivery system can include two IDE arrays as illustrated in FIG. 1B. A signal generator such as a multi-channel function generator (e.g., a TGA1244 signal generator, Thurlby Thandar Instruments Limited, Cambridgeshire, United Kingdom) can be utilized to generate an electrical signal containing three distinct frequencies. An optimal high (for example, 5000 Hz) and low (for example, 10 Hz) frequency can be applied to second IDE array 138, or the distal IDE, alternating between electrode components every minute, while other (for example, 400 Hz and 5000 Hz) frequencies can be applied to first IDE array 136, or the proximal IDE array. The applied field can be 5 Vpp/mm, as a representative embodiment, in amplitude, and a digital oscilloscope can be used to monitor the frequency and waveform of the applied signals during the experiments.

In some embodiments, the intraoral delivery system utilizes the DEP/ACEO combination to deliver fluoride up to 100-300 μm deep, whereas conventional topical fluoride application effectively delivered fluoride to a 20 μm depth ($P<0.05$). Compared to passive diffusion, fluoride uptake in enamel can be significantly higher when treated by the DEP/ACEO combination at 10-300 μm depths ($P<0.05$). Experimental observations showed that DEP/ACEO forces can drive the fluoride substantially deeper into the enamel with a difference in uptake 1575 ppm higher than diffusion at 100 μm depth; 6 times (582%) higher at 50 μm depth (average particle uptake [$\bar{x}$]=2892 ppm/409 ppm); 5 times (515%) higher at 20 μm depth ([$\bar{x}$]=3692 ppm/600 ppm); and 7 times (720%) higher at 10 μm depth ([$\bar{x}$]=9467 ppm/1154 ppm). Average fluoride uptake with DEP/ACEO combination was 742 ppm at 200 μm depth, reaching appreciable levels (375 ppm) at 300 μm depth during the allotted treatment time.

In some embodiments, desired frequencies for a given active agent, such as but not limited to the 10 Hz and 5000 Hz frequencies for fluoride, can be applied in succession to each component of second IDE array 138, or the distal IDE according to FIG. 1B, alternating between frequencies at one minute intervals; while 400 Hz and 5000 Hz can be applied in succession to each component of first IDE array 136, or the proximal IDE in the same manner. Assuming that 5000 Hz causes pDEP (positive-DEP) and 10 Hz causes the nDEP (negative-DEP), the fluoride particles can be trapped by the pDEP at the edges of one or the other distal component electrodes at 5000 Hz and may then be driven away and through the slots towards the proximal IDE (first IDE 136) by nDEP at 10 Hz. In some embodiments, the 10 Hz and 5000 Hz frequencies can alternate between component electrodes of the distal IDE every minute. Notably, this change in frequency can cause the particles (e.g., fluoride particles) to be trapped at the edges of the distal IDE at various times, which can cause the particles to be continuously pushed away and travel through the slots towards the proximal IDE (first IDE 136). As the 400 Hz and 5000 Hz frequencies alternate between both components of the proximal IDE at one minute intervals, the 400 Hz frequency can cause a reduction of pDEP to induce ACEO at each component every other minute. Thus, the fluoride particles can be continually pushed away from the edges (where they had originally accumulated due to pDEP) towards the center of the electrode and up into the enamel by convection throughout the allotted treatment time.

In some embodiments, different particle movements can occur when each frequency was applied in sequence to the same electrode at different times. For example, fluoride particles can line up in chains along the electrode edge when 5000 Hz was applied and where the field strength was expected to be the strongest (posDEP). When the 5000 Hz frequency was stopped and 10 Hz was applied, the fluoride particles can be driven away from the electrode edge, indicating nDEP. Furthermore, when 10 Hz was stopped and 400 Hz applied, the fluoride particles can be dragged toward the center and above the electrode in a convective-like pattern. This can suggest that the 400 Hz frequency induced ACEO. The coplanar IDE arrays utilized here can use AC current without DC bias to avoid potential bulk fluid flow that may cause the tooth to swell. In this manner, applying an electrical field at 400 Hz frequency can produce a mild vortex without net fluid flow which, in effect, can convey more fluoride particles towards the enamel pores and, thereby, increase fluoride uptake. Assuming that the fluoride particles can become deposited at the enamel surface via this mechanism, the particles can react with hydroxyapatite to form sub-micron aggregates.

The fluoride uptake by human tooth enamel after a four minute application of APF gel has been known to be about 1763-3405 ppm at 5 μm depth. In comparison, fluoride uptake at 10 μm by diffusion after twenty minutes can be 1154 ppm, but can be 9467 ppm with the DEP/ACEO combination treatment. As such, DEP/ACEO combination fluoride treatment can be a useful tool for the prevention of cavities. A fluoride reservoir deep within the tooth can provide a long term source for remineralization. Fluoride application with a combined DEP/ACE technique can allow penetration into enamel as deep as 200-300 µm to create such a reservoir. Considering current remineralization strategies aim to create a surface reservoir, a fluoride reservoir deep within the enamel can be drawn from over time to replenish a fluoride-depleted surface layer.

Referring again to FIG. 1E, a representative approach for preparing an IDE in accordance with the present disclosure is as follows. Pyralux 9121R (DuPont, Wilmington, Del., United States of America), double sided copper cladded polyimide film was used for the fabrication of the inter-digit electrode. Fourteen teeth of a complimentary electrode are interdigitated with another identical electrode on a pitch of 1 mm. Two layers of interdigitated electrodes are separated by the insulating polyimide film thickness itself (50 µm). Fabrication steps: 1) The film was tapped on supporting wafer and cleaned with acetone and methanol first and then spin coated with AZ1518 positive photoresist (AZ Electronic Materials USA Corporation, Somerville, N.J., United States of America). 2) Photoresist was developed for desired pattern by exposing under the UV light through the transparency mask for 8 seconds and then developed in the developer solution. 3) The same process was repeated on the other side of the film and exposed under UV light such that the pattern to be exactly aligned with the IDE pattern on the other side of the film. 4) Exposed copper was then chemically etched in ferric chloride solution for approximately 25 minutes to have alternative electrode pattern (250 µm wide, 35 µm thick and at 1 mm pitch, 28 total electrode teeth) and rinsed thoroughly under running DI water for 5 minutes. The gap of 500 µm between any two electrode teeth was created using laser ablation technique. After laser ablation, the IDE was ultrasonically cleaned in acetone and DI water for 5 minutes each, respectively. The electrode was cleaned in RIE plasma etching machine to remove any organic contamination before gold plating on the surface. Adhesion layer of nickel was electroplated first on copper surface at 60° C. on hot stirrer plate. Nickel surface was activated by nickel activator solution before gold plating on it. Cobalt hardened acid gold electroplating solution (24K bright gold plating solution) (Gold plating services, University of Tennessee, Knoxville, Tenn., United States of America) was used to electroplate IDE electrodes to make it corrosion resistant and biocompatible. The IDE was immersed in gold plating solution at 37° C. and 6A per square feet was applied for 8 minutes in order to get 1 µm of uniform old layer on IDE.

Figure 4B:
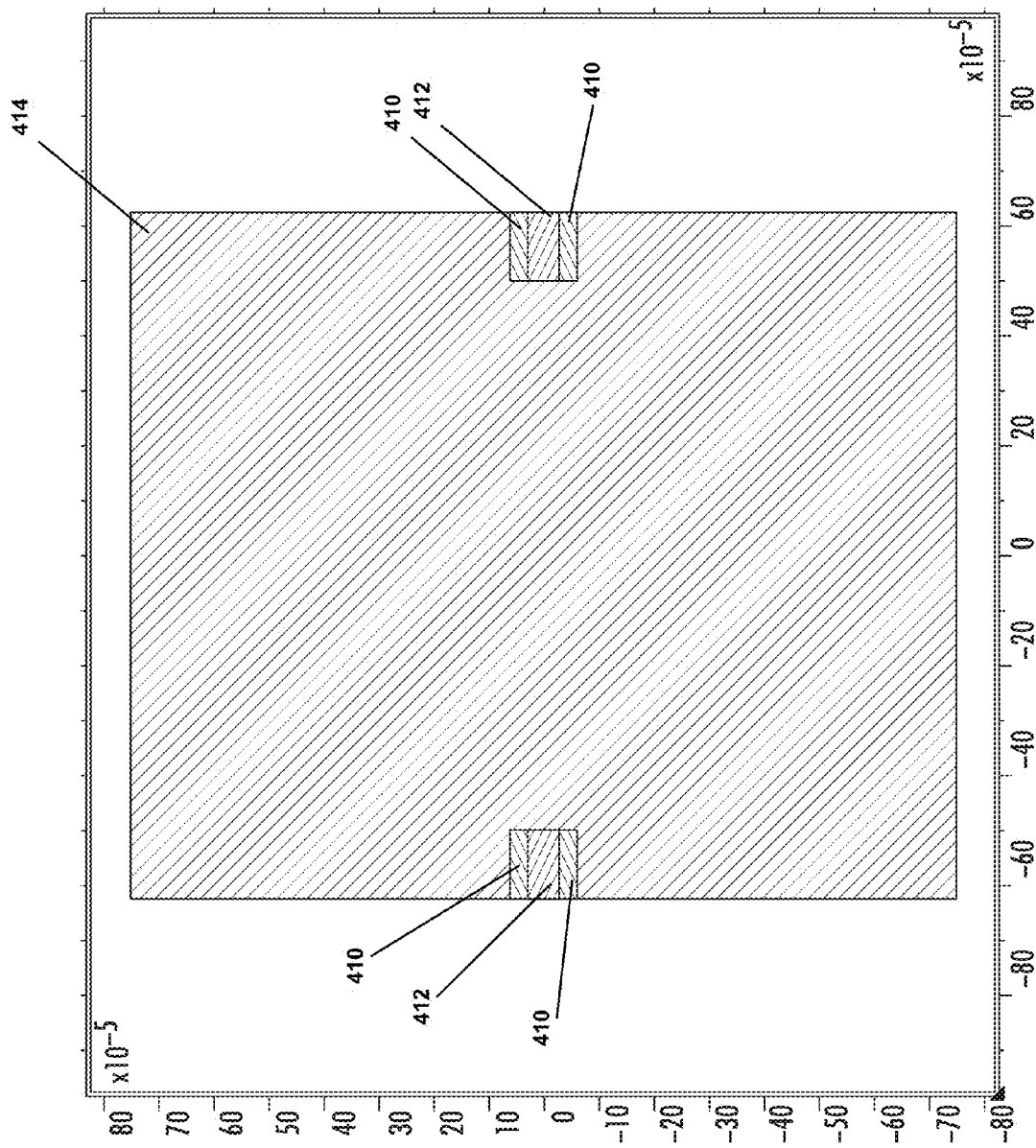
FIG. 4B illustrates an exemplary COMSOL simulation configuration in accordance with embodiments of the subject matter described herein.

In some embodiments, the DEP and ACEO forces can be simulated and calculated using COMSOL Multiphysics finite element analysis software version 4.2a (COMSOL Inc., Burlington, Mass., United States of America). In some embodiments, the COMSOL simulation can be performed in a simulation box of 130 µm×150 µm in size. A cross section of one set of electrode can be modeled, as the structure is repetitive in nature. Four electrodes can be excited independently. In case of cross-planar excitation, the top electrodes are excited with a positive potential whereas the bottom electrodes are at ground potential. In case of coplanar excitation, the left electrodes can be excited with positive potential, whereas the right electrodes can be connected to a ground potential. FIG. 4B illustrates an exemplary COMSOL simulation configuration in accordance with embodiments of the subject matter described herein. Where on each side of the figure, two electrodes 410 are insulated by a polyimide layer 412 and surrounded by water 414.

Figure 4C:
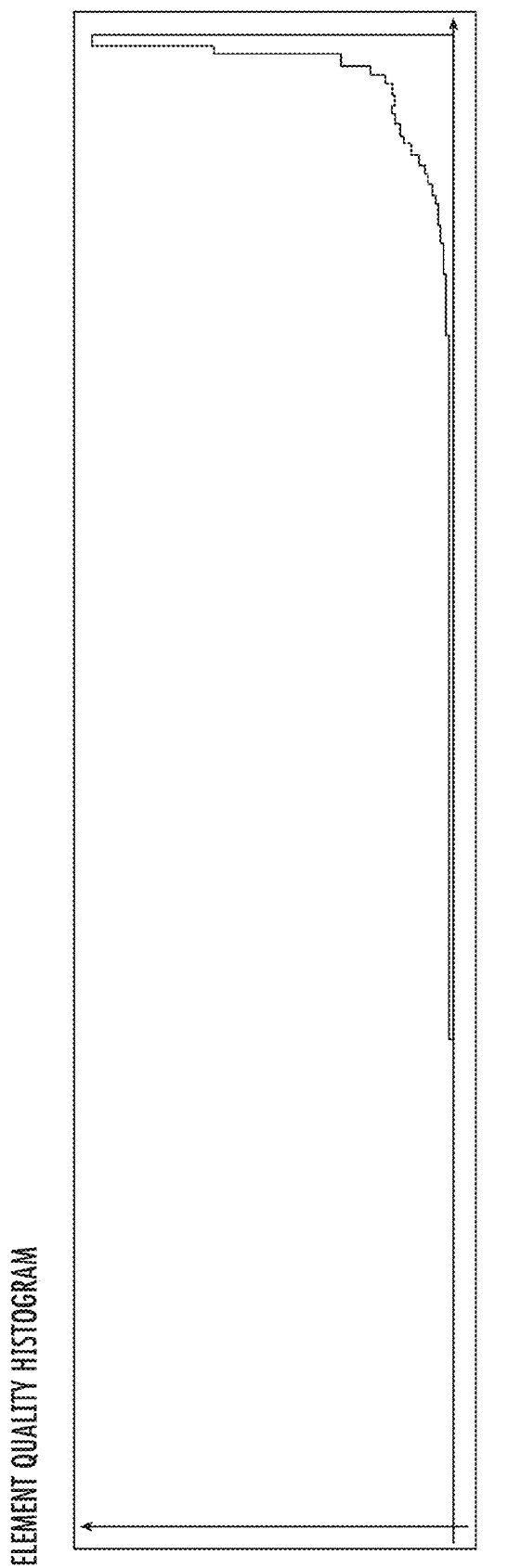
FIG. 4C illustrates an exemplary histogram of element sizes of a COSMOL simulation in accordance with embodiments of the subject matter described herein.

In some embodiments, as illustrated in FIG. 4C, mess size can be originally selected as the maximum preset values (extremely high). After an initial meshing, each domain can be re-meshed with a 1.2 scale factor. As such, the resultant mesh can have 73168 elements, with a minimum element quality of 0.3288, an average element quality of 0.9447. Furthermore, the mesh can include 70416 triangular elements, 2752 quadrilateral elements, 2584 edge elements, and/or 20 vertex elements.

Figure 4D:
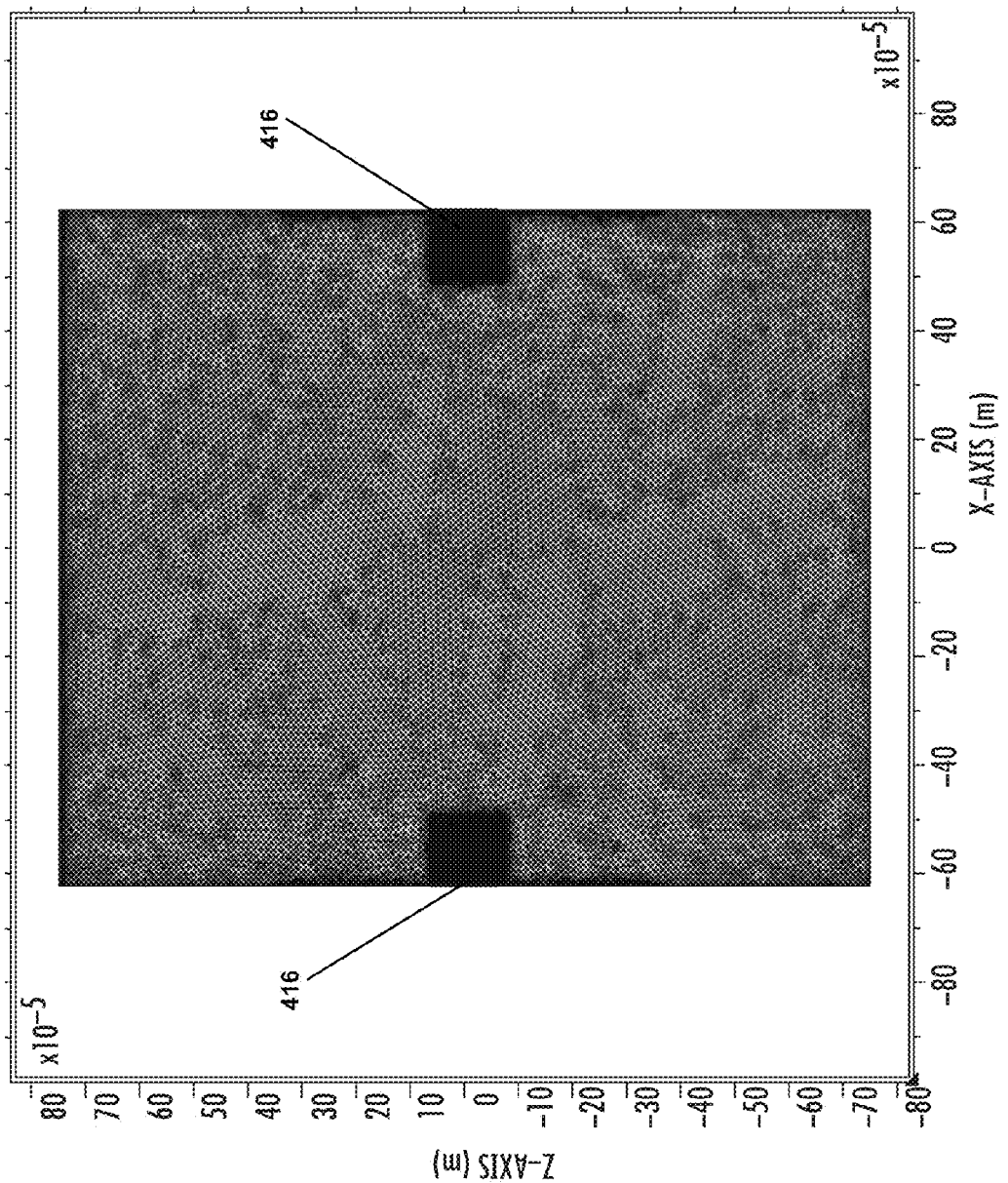
FIG. 4D illustrates another exemplary COMSOL simulation configuration in accordance with embodiments of the subject matter described herein.
Figure 4E:
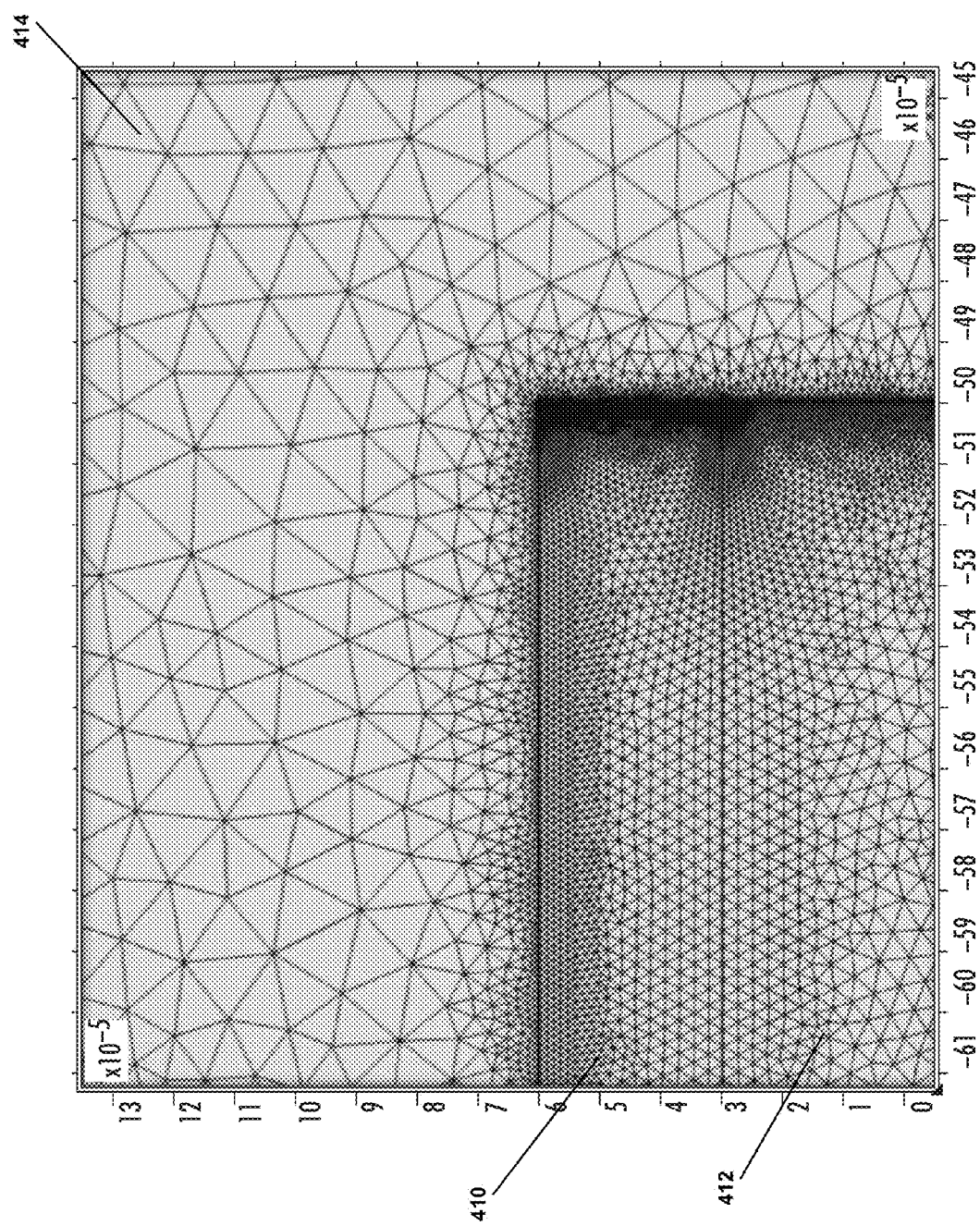
FIG. 4E illustrates an exemplary close up view of a COMSOL simulation configuration in accordance with embodiments of the subject matter described herein.

FIG. 4D is an exemplary example of a mesh of the complete system as shown in FIG. 4B. As illustrated in FIG. 4D, various elements can be meshed between the simulated IDE elements 416. Furthermore, FIG. 4E illustrates an exemplary close up view of a top corner of an electrode in accordance with embodiments of the subject matter described herein. As shown in FIG. 4E, solver physics can be enabled by Electric currents (emdc) and Laminar flow (mmglf), where discretizations can be based on physics settings. For example, stationary solver of relative tolerance of 0.001 can be selected with an automatic linearity option. The number of iterations can be set at 5, with estimated error of $2.1 \times 10^{-12}$ and step-size of $5.9 \times 10^{-8}$.

In some embodiments, electric current physics can be simulated for all domains, whereas Laminar flow can be simulated for only fluidic domain. Furthermore, energy conservation can be selected for all domains, with the following boundary conditions:
1. Electrical insulation for periodic boundaries.
2. Terminals for non-periodic boundaries.
3. Point wise constraint for one of the periodic boundaries.
4. Wall for all solid interfaces as well as non-periodic boundaries.
5. Open fluidic boundaries for all periodic boundaries.
6. Point wise constraint for one of the periodic boundaries.

FIGS. 4 F-I show two sets of simulation results obtained for coplanar and cross-planar excitation of $5V_{peak}$. In some embodiments, the periodic nature of the IDE configuration can be exploited to simulate a two-dimensional section of the DEP/ACE device consisting of IDE arrays. The simulation region (1.25 mm×1 mm) can be a cross-section of a pair of electrode assemblies with interstitial space in the middle region. Each electrode assembly can be composed of a top and bottom electrode, separated by a layer of polyimide. The remaining simulation region is filled with water.

Figure 4F:
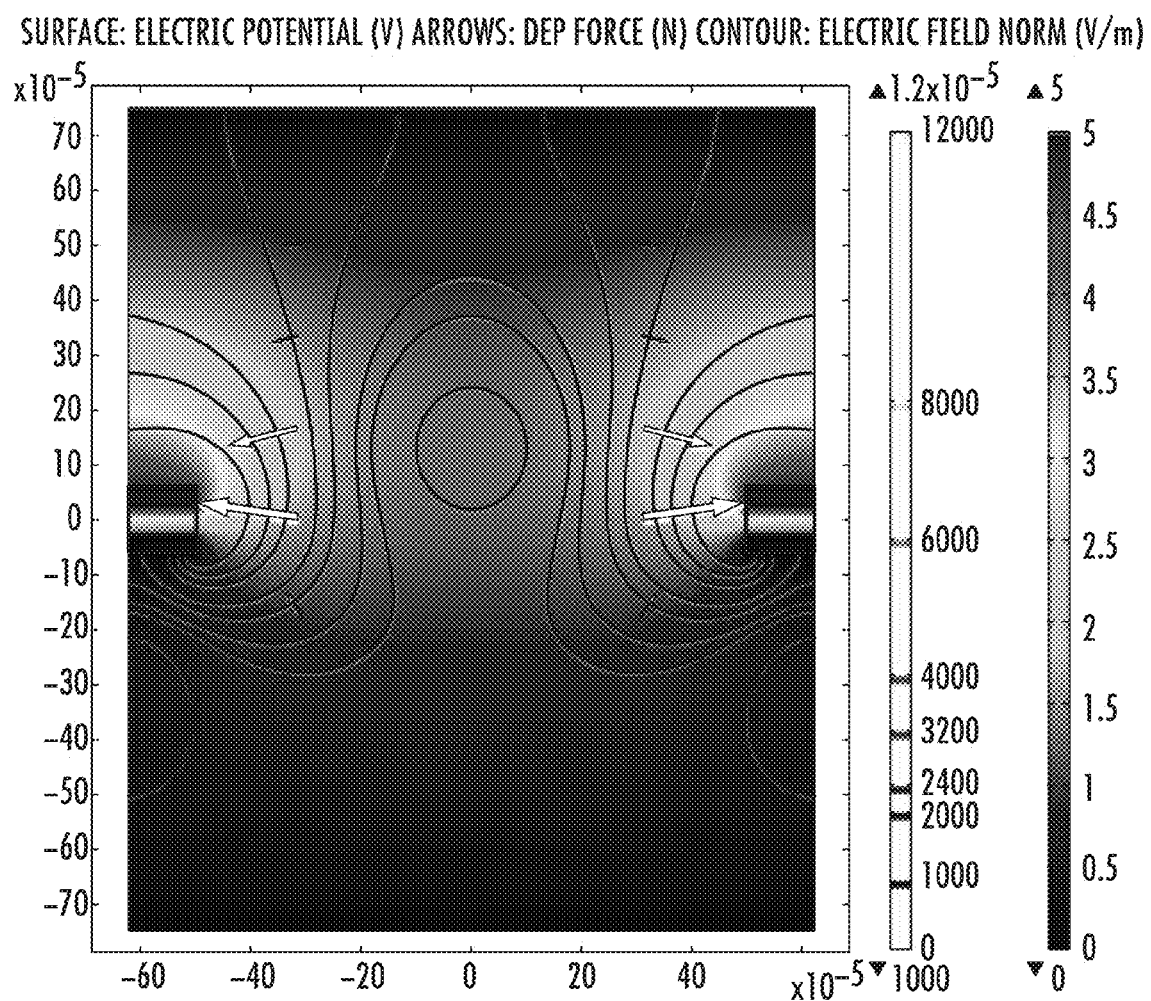
FIGS. 4F to 4I are exemplary illustrations of simulated DEP and ACE fields in accordance with embodiments of the subject matter described herein.
Figure 4G:
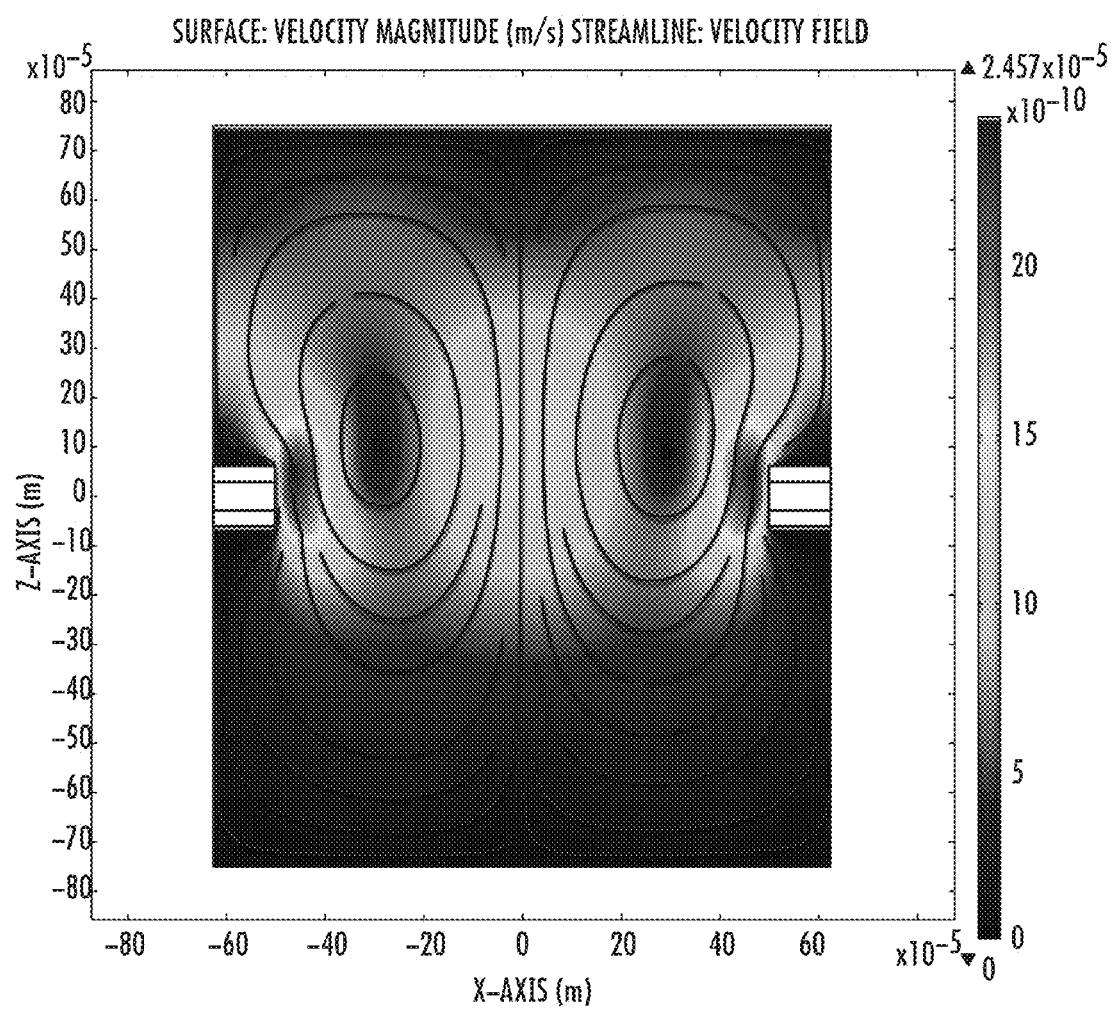
Figure 4H:
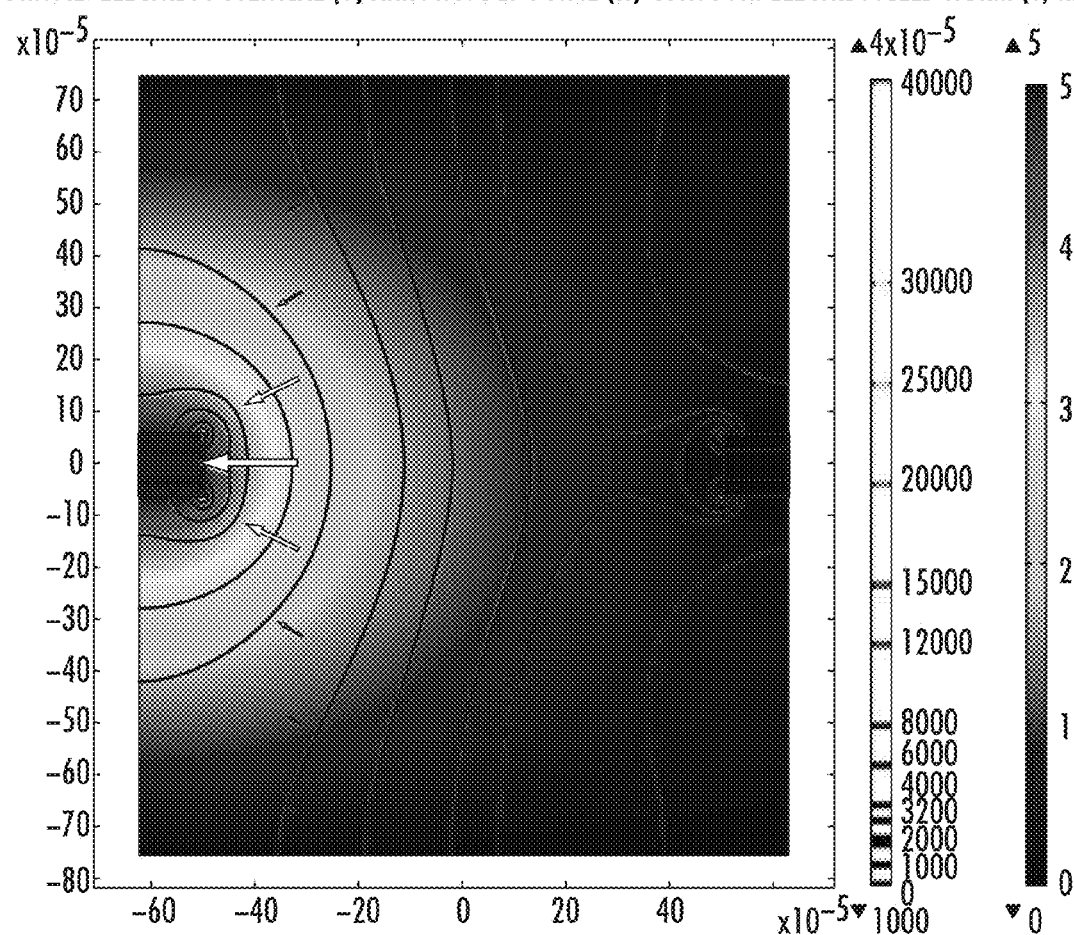
Figure 4I:
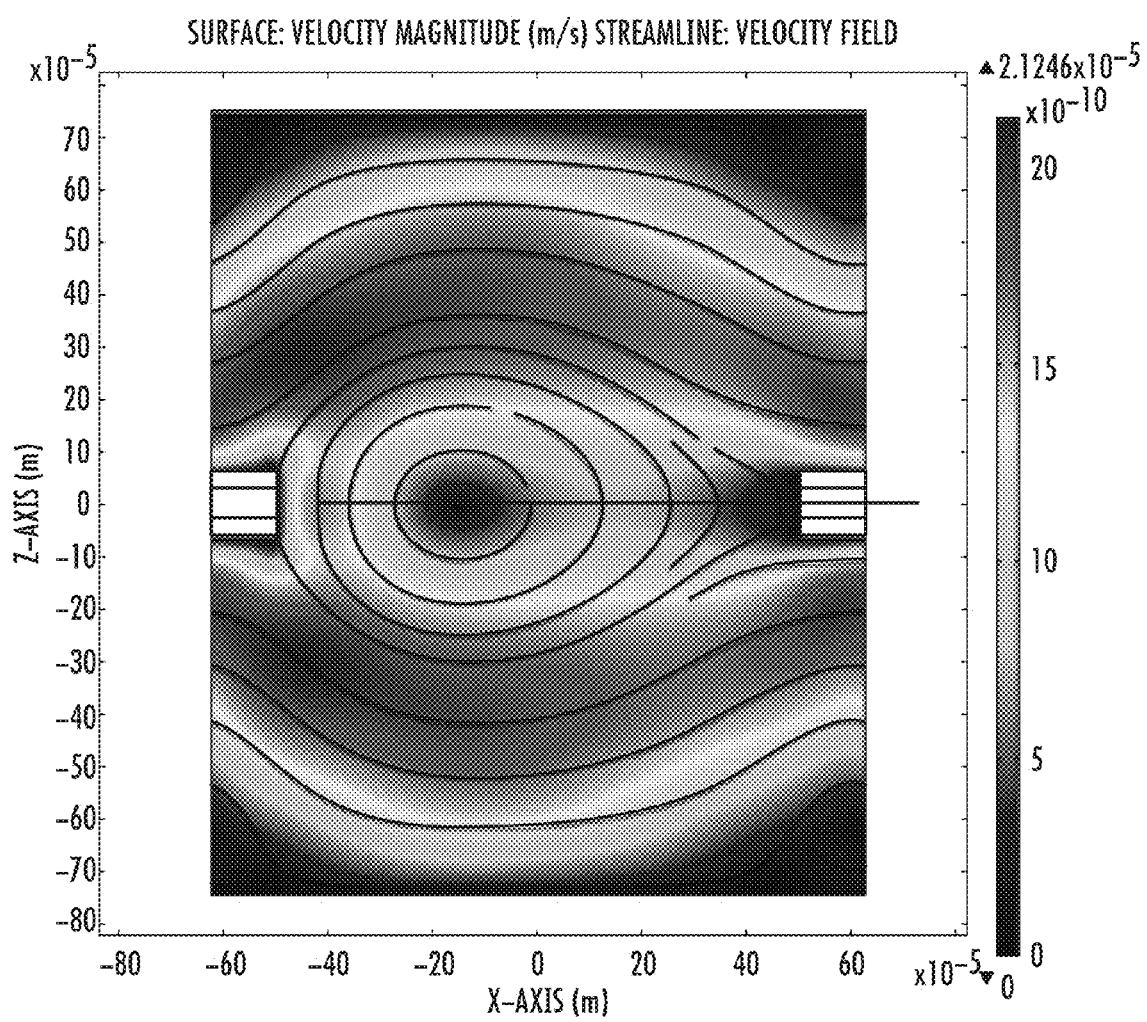

An integrated material database can be used to induce excitation at the boundaries of the electrodes, assigning the top and the bottom boundary of the simulation region as terminals, and specifying the boundaries on both sides as periodic. Electric current and fluidic flow physics can be included in the simulation with General Physics controlled extra fine mesh settings. FIGS. 4F and 4H show the electric potential distribution, DEP force and the developed electric fields, while FIGS. 4G and 4H depict the ACE velocity magnitudes and fields with the application of a normalized excitation potential between coplanar or cross-planar electrodes.

FIG. 4J illustrates DEP forces at various distances from an electrode in accordance with embodiments of the subject matter described herein. As shown in FIG. 4J, both vertical and horizontal DEP forces are strongest 1 micron away from the electrode, and decreases significantly moving away from the electrode.

Figure 5:
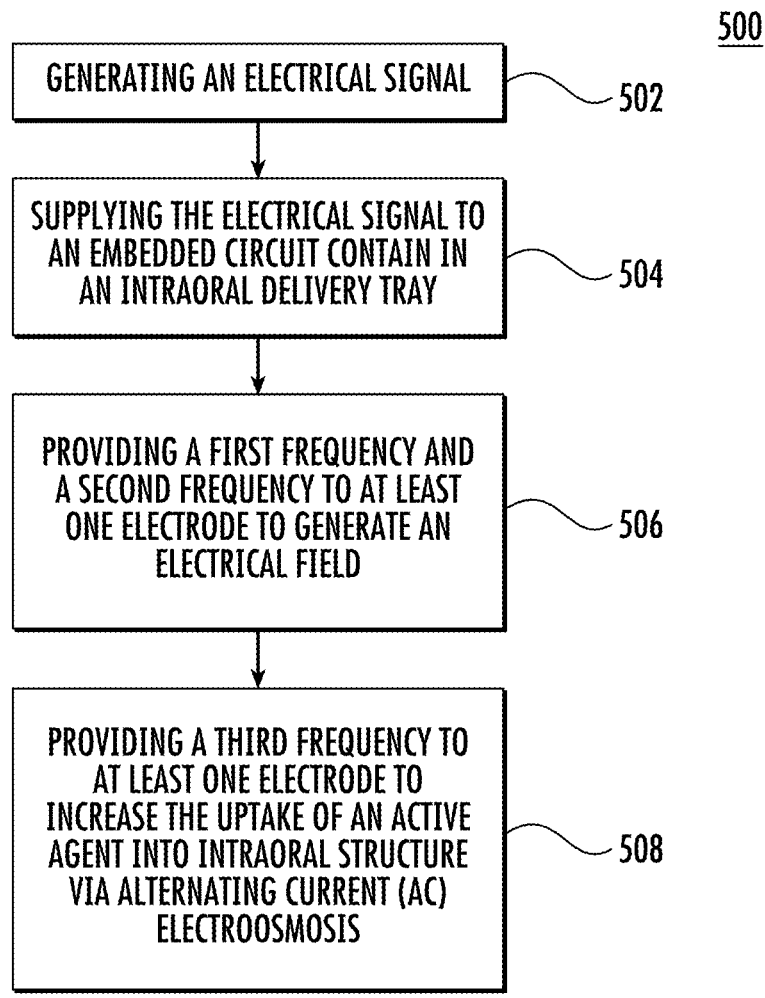
FIG. 5 is a flow chart illustrating an exemplary method for delivering an active agent into an intraoral structure in accordance with aspects of the subject matter described herein.

FIG. 5 is a flow chart illustrating an exemplary method, generally designated 500, for delivering an active agent into an intraoral structure in accordance with aspects of the subject matter described herein. At step 502, an electrical signal that includes a first frequency, a second frequency, and a third frequency can be generated. In some embodiments, a signal generator can generate an electrical signal including an optimal high frequency and an optimal low frequency for generating DEP electrical fields. Furthermore, the electrical signal can also include an AECO frequency configured to facilitate drug agent (e.g. fluoride particles) diffusion into tooth enamel or other intraoral structure utilizing electroosmosis forces.

At step 504, the generated electrical signal can be supplied to an embedded circuit contained in an intraoral delivery tray. In some embodiment, the intraoral delivery tray can include two IDE arrays and a control circuit. The optimal high and low frequencies can be supplied to a first IDE array, and the optimal high and AECO frequencies can be supplied to a second IDE array. In some other embodiment, the intraoral delivery tray can include two IDE arrays and a control circuit. The optimal high and low frequencies can be electrically coupled to a first and second IDE array, and the AECO frequency can be couple to a third IDE array.

At step 506, a first and a second frequency can be provided to at least one electrode to generate an electrical field that electrically motivates the active agent suspended in a fluid medium contained in the intraoral delivery tray toward the intraoral structure via dielectrophoresis. In some embodiments, an optimal high and an optimal low frequency can be electrically coupled to the IDEs to induce an electrical field perpendicular to the tooth enamel. This electrical field can induce fluoride particles to motion toward the enamel surface using dielectrophoretic motion of fluoride particles via the viscous interaction between the particles and the surrounding fluid (e.g. gel), which can primarily comprise water. Dielectrophoresis is the motion of small particles in a surrounding medium, when exposed to a non-uniform electric field, due to the interaction between the induced dipole on the particles and the electric field. As the result of viscosity, the fluid surrounding the particles can be dragged to move in the same direction as the particles, giving rise to an effective pumping action.

At step 508, a third frequency can be provided to an electrode to increase the uptake of the active agent into intraoral structure via alternating current electroosmosis. ACEO is based on the ion migration within a nanometer layer of charges/ions at the interface of the electrolytes and solids (double layer). In ACEO, the charges in the double layer can be induced by an AC potential, and tangential E-fields can also form from the same voltage source. By adjusting the amplitude and frequency of AC signals, a variety of directed surface flows can be produced on electrodes to manipulate and transport particles. In some embodiments, a third frequency of the electrical signal can be modulated to sufficiently increase conductivity, decrease electrical resistivity, increase permeability of the intraoral structure (e.g., bone, periodontal ligament, etc.), and/or modulated to sufficiently generate an electrical double layer that will induce a Coulomb force to actuate the flow of the agent into a target site via AC electroosmosis.

In some embodiments, a third frequency of the electrical signal is sufficient to increase conductivity of a particle (e.g., active agent particle), and/or is sufficient to generate an electrical double layer that will induce a Coulomb force to actuate the flow of the agent into a target site via AC electroosmosis. In some embodiments, a third frequency can be modulated to regulate desired depth of penetration into the enamel. This frequency can be connected to an IDE array and configured to alternate between electrode components every minute to facilitate the deposition of fluoride particle deep (e.g. 100 μm) into the tooth's enamel.

It will be understood that various details of the subject matter described herein may be changed without departing from the scope of the subject matter described herein. Furthermore, the foregoing description is for the purpose of illustration only, and not for the purpose of limitation, as the subject matter described herein is defined by the claims as set forth hereinafter.

What is claimed is:

1. A method for delivering an active agent into an intraoral structure, the method comprising:
   generating an electrical signal that includes a first frequency, a second frequency, and a third frequency;
   supplying the electrical signal to an embedded circuit contained in an intraoral delivery tray, wherein the embedded circuit comprises at least one electrode that includes projections adapted for positioning proximally to a surface of an intraoral structure;
   providing the first frequency and the second frequency to the at least one electrode to generate an electrical field that electrically motivates the active agent suspended in a fluid medium contained in the intraoral delivery tray toward the intraoral structure via dielectrophoresis (DEP), wherein the first frequency sorts the active agent from other fluid components via positive DEP and the second frequency compels the active agent to exhibit motion away from the at least one electrode and toward the intraoral structure via negative DEP; and
   providing the third frequency to the at least one electrode to increase uptake of the active agent into the intraoral structure via alternating current (AC) electroosmosis.

2. The method of claim 1 wherein the intraoral structure includes at least one tooth structure, an intraoral mucosal structure, supporting structure, boney structure, or soft tissue structure.

3. The method of claim 1 wherein the first frequency, the second frequency, and third frequency are simultaneously provided to the at least one electrode.

4. The method of claim 1 wherein the first frequency of the electrical signal satisfies a Clausius-Mossotti factor in a DEP force equation that results in a value greater than zero and the second frequency of the electrical signal satisfies a Clausius-Mossotti factor in a DEP force equation that results in a value less than zero.

5. The method of claim 1 wherein the third frequency of the electrical signal generates convective vortices perpendicular to the electrode to actuate the flow of the active agent within the intraoral structure via AC electroosmosis.

6. The method of claim 5 wherein the third frequency is modulated to regulate the transport and concentration of the active agent into varying depth levels of the intraoral structure.

7. The method of claim 6 wherein the varying depth levels of the intraoral structure include a range of 1 micron to full thickness of an enamel, dentin, cementum, or pulp of at least one tooth.

8. The method of claim 1 wherein the active agent includes fluoride.

9. The method of claim 1 wherein the active agent is a drug agent.

10. The method of claim 9 wherein the drug agent includes an antibiotic, an anesthetic agent, an anti-inflammatory agent, an analgesic, a remineralizing agent, a tooth regenerative factor, a restorative or bonding agent, an immunomodulating agent, a hormone or growth factor, an antimicrobial agent, or a combination thereof.

11. The method of claim 1 comprising using a circuit analyzer to analyze electrical parameters of the embedded circuit in response to the electrical signal.

12. The method of claim 1 wherein the embedded circuit includes a flexible printed circuit board (PCB) material, a silk material or graphene.

13. The method of claim 1 wherein the electrical signal includes an alternating current (AC) signal or an AC voltage wave function that is sinusoidal, square, triangular, or pulse.

14. The method of claim 1 wherein each of the first frequency and the second frequency of the electrical signal is determined based on a dielectric profile associated with the active agent.

15. The method of claim 14 wherein each of the first frequency and the second frequency is between 0 hertz and 100,000 hertz.

16. The method of claim 1 wherein the third frequency of the electrical signal is sufficient to increase conductivity, decrease electrical resistivity, increase permeability of the intraoral structure, and/or is sufficient to generate an electrical double layer that will induce a Coulomb force to actuate the flow of the agent into a target site via AC electroosmosis.

17. The method of claim 1 wherein the third frequency is between 0 hertz and 500 hertz, or a frequency sufficient to induce fluid movement without invoking an AC electrothermal effect.

18. The method of claim 1 further comprising utilizing a wireless reader device to wirelessly supply electrical power to a signal generator module, wherein the signal generator module is included in the intraoral delivery tray.

19. The method of claim 18 wherein the wireless reader includes a radio frequency identification (RFID) reader.

20. The method of claim 18 wherein the wireless reader inductively establishes a wireless connection with an antenna included on the embedded circuit.

21. The method of claim 20 wherein the embedded circuit converts the supplied electrical power into an alternating current (AC) output that powers the signal generator module.

22. An intraoral fluidic delivery system, the system comprising:

an intraoral delivery tray including an embedded circuit comprising at least one electrode, wherein the at least one electrode comprises a portion that includes projections adapted for positioning proximally to a surface of an intraoral structure; and a signal generator module configured to provide an electrical signal to the embedded circuit, wherein the electrical signal includes a first frequency, a second frequency, and a third frequency, wherein the first frequency and the second frequency increase molecular availability and mobility of an active agent suspended in a fluid medium contained in the intraoral delivery tray via dielectrophoresis (DEP), wherein the first frequency sorts the active agent from other fluid components via positive DEP and the second frequency compels the active agent to exhibit motion away from the at least one electrode and toward the intraoral structure via negative DEP, and wherein the third frequency increases uptake of the active agent by the intraoral structure via alternating current (AC) electroosmosis.

23. The system of claim 22 wherein the intraoral structure includes at least one tooth structure, an intraoral mucosal structure, supporting structure, boney structure, or soft tissue structure.

24. The system of claim 22 wherein the first frequency, the second frequency, and third frequency are simultaneously provided to the at least one electrode.

25. The system of claim 22 wherein the first frequency is defined by a value where the real part of the Clausius-Mossotti factor in a DEP force equation is greater than zero and the second frequency of the electrical signal satisfies a Clausius-Mossotti factor in a DEP force equation that results in a value less than zero.

26. The system of claim 22 wherein the third frequency of the electrical signal generates convective vortices that pump and transport the active agent within the intraoral structure via AC electroosmosis.

27. The system of claim 22 wherein the third frequency is modulated to regulate the concentration and transport of the active agent into varying depth levels of the intraoral structure.

28. The system of claim 27 wherein the varying depth levels of the intraoral structure include a range of 1 micron to full thickness of an enamel, dentin, cementum, or pulp of at least one tooth.

29. The system of claim 22 wherein the active agent includes fluoride.

30. The system of claim 22 wherein the active agent is a drug agent.

31. The system of claim 30 wherein the drug agent includes an antibiotic, an anesthetic agent, an anti-inflammatory agent, an analgesic, a remineralizing agent, a tooth regenerative factor, a restorative or bonding agent, an immunomodulating agent, a hormone or growth factor, an antimicrobial agent, or a combination thereof.

32. The system of claim 22 comprising using a circuit analyzer to analyze electrical parameters of the embedded circuit in response to the electrical signal.

33. The system of claim 22 wherein the embedded circuit includes a flexible printed circuit board (PCB) material, a silk material or graphene.

34. The system of claim 22 wherein the electrical signal includes an alternating current (AC) signal or an AC voltage wave function that is a sinusoidal, square, triangular or pulse signal.

35. The system of claim 22 wherein each of the first frequency and the second frequency of the electrical signal is determined based on a dielectric profile associated with the active agent.

36. The system of claim 35 wherein each of the first frequency and the second frequency is between 0 hertz and 100,000 hertz.

37. The system of claim 22 wherein the third frequency of the electrical signal is sufficient to increase conductivity, decrease electrical resistivity, increase permeability of the intraoral structure, and/or is sufficient to generate an electrical double layer that will induce a Coulomb force to actuate the flow of the agent into the target site via AC electroosmosis.

38. The system of claim 37 wherein the third frequency is between 0 hertz and 500 hertz, or a frequency sufficient to induce fluid movement without invoking an AC electrothermal effect.

39. The system of claim 22 further including a wireless reader configured to wirelessly supply electrical power to the signal generator module, wherein the signal generator module is included in the intraoral delivery tray.

40. The system of claim 39 wherein the wireless reader includes a radio frequency identification (RFID) reader.

41. The system of claim 39 wherein the wireless reader inductively establishes a wireless connection with an antenna included on the embedded circuit.

42. The system of claim 41 wherein the embedded circuit converts the supplied electrical power into an alternating current (AC) output that powers the signal generator module.

43. A method for delivering an active agent into an intraoral structure, the method comprising:

generating an electrical signal that includes a first frequency, a second frequency, and a third frequency;

supplying the electrical signal to at least one electrode that includes projections adapted for positioning proximally to a surface of an intraoral structure;

providing the first frequency and the second frequency to the at least one electrode to generate an electrical field that electrically motivates the active agent toward the intraoral structure via dielectrophoresis (DEP), wherein the first frequency sorts the active agent from other fluid components via positive DEP and the second frequency compels the active agent to exhibit motion away from the at least one electrode and toward the intraoral structure via negative DEP; and providing the third frequency to the at least one electrode to increase uptake of the active agent into the intraoral structure via alternating current (AC) electroosmosis.

44. An intraoral fluidic delivery system, the system comprising:

at least one electrode, wherein the at least one electrode comprises a portion that includes projections adapted for positioning proximally to a surface of an intraoral structure; and a signal generator module configured to provide an electrical signal to at least one electrode, wherein the electrical signal includes a first frequency, a second frequency, and a third frequency, wherein the first frequency and the second frequency increase molecular availability and mobility of an active agent via dielectrophoresis (DEP), wherein the first frequency sorts the active agent from other fluid components via positive DEP and the second frequency compels the active agent to exhibit motion away from the at least one electrode and toward the intraoral structure via negative DEP, and wherein the third frequency increases uptake of the active agent by the intraoral structure via alternating current (AC) electroosmosis.

* * * * *